US012759967B2

(12) United States Patent
Schaub et al.

(10) Patent No.: US 12,759,967 B2
(45) Date of Patent: Oct. 13, 2026

(54) PROCESS FOR PREPARING SUBSTITUTED BIPHENYLS VIA SUZUKI COUPLING OF ARYL-CHLORIDES

(71) Applicant: BASF SE, Ludwigshafen (DE)

(72) Inventors: Thomas Schaub, Ludwigshafen (DE); Desislava Slavcheva Petkova, Ludwigshafen (DE); Jochen Dietz, Ludwigshafen (DE); Roland Goetz, Ludwigshafen (DE); A. Stephen K. Hashmi, Heidelberg (DE); Patrizio Orecchia, Heidelberg (DE)

(73) Assignee: BASF SE, Ludwigshafen (DE)

( * ) Notice: Subject to any disclaimer, the term of this patent is extended or adjusted under 35 U.S.C. 154(b) by 447 days.

(21) Appl. No.: 18/562,130

(22) PCT Filed: May 10, 2022

(86) PCT No.: PCT/EP2022/062558
§ 371 (c)(1),
(2) Date: Nov. 17, 2023

(87) PCT Pub. No.: WO2022/243099
PCT Pub. Date: Nov. 24, 2022

(65) Prior Publication Data
US 2024/0270677 A1 Aug. 15, 2024

(30) Foreign Application Priority Data
May 19, 2021 (EP) .................................... 21174585

(51) Int. Cl.
*C07C 201/12* (2006.01)
*B01J 31/24* (2006.01)
*C07D 213/82* (2006.01)
*C07D 231/40* (2006.01)

(52) U.S. Cl.
CPC ............. *C07C 201/12* (2013.01); *B01J 31/24* (2013.01); *C07D 213/82* (2013.01); *C07D 231/40* (2013.01)

(58) Field of Classification Search
CPC ..... C07C 201/12; C07C 69/76; C07D 213/82; C07D 231/40; B01J 21/24
See application file for complete search history.

(56) References Cited

U.S. PATENT DOCUMENTS 7,772,446 B2 * 8/2010 Engel .................... C07C 209/68 564/305
9,868,694 B2 1/2018 Dockner et al.

FOREIGN PATENT DOCUMENTS

WO WO-2006/092429 A1 9/2006
WO WO-2015/011032 A1 1/2015
WO WO-2018/149813 A1 8/2018

OTHER PUBLICATIONS

Charbonneau, et al., "Support-Free Palladium—NHC Catalyst for Highly Recyclable Heterogeneous Suzuki-Miyaura Coupling in Neat Water", Organometallics, vol. 33, Issue 22, Nov. 2014, pp. 6544-6549.
Firouzabadi, et al., "Agarose hydrogel as an effective bioorganic ligand and support for the stabilization of palladium nanoparticles. Application as a recyclable catalyst for Suzuki-Miyaura reaction in aqueous media", RSC Advances, vol. 1, Issue 6, Sep. 5, 2011, pp. 1013-1019.
Yamada, et al., "Self-Assembled Poly(imidazole-palladium): Highly Active, Reusable Catalyst at Parts per Million to Parts per Billion Levels", Journal of the American Chemical Society, vol. 134, Issue 6, Jan. 16, 2012, pp. 3190-3198.
Zhang, et al., "PEG Click-Triazole Palladacycle: An Efficient Precatalyst for Palladium-Catalyzed Suzuki-Miyaura and Copper-free Sonogashira Reactions in Neat Water", Chinese Journal of Chemistry, vol. 33, Issue 7, Jul. 1, 2015, pp. 705-710.
International Search Report and Written Opinion for PCT Patent Application No. PCT/EP2022/062558, Issued on Sep. 12, 2022.
International Preliminary Report on Patentability (Chapter II) with annex for PCT Patent Application No. PCT/EP2022/062558, dated Mar. 17, 2023.

* cited by examiner

*Primary Examiner* — Yate' K Cutliff
(74) *Attorney, Agent, or Firm* — MARSHALL, GERSTEIN & BORUN LLP

(57) ABSTRACT

A process for preparing substituted biphenyls of the formula (I) which comprises reacting a compound of the formula (II) in the presence of a base and of a palladium catalyst, with an organoboron compound of the formula (IV).

(I)

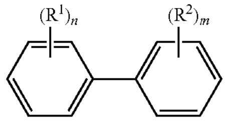

(II)

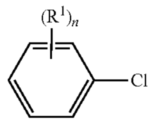

(IV)

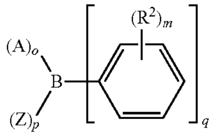

11 Claims, 2 Drawing Sheets

PROCESS FOR PREPARING SUBSTITUTED BIPHENYLS VIA SUZUKI COUPLING OF ARYL-CHLORIDES

CROSS-REFERENCE TO RELATED APPLICATIONS

This is the U.S. national phase of International Application No. PCT/EP2022/062558, filed May 10, 2022, which claims the benefit of European Patent Application No. 21174585.6, filed May 19, 2021.

Functionalized biphenyl compounds are of great interest especially as pharmaceuticals and pesticides, and as precursors of such active ingredients. For instance, 2-nitro and 2-aminobiphenyls are important precursors for aryl- and heteroarylcarboxamides which find use as fungicides, and for which Boscalid®, fluxapyroxad, bixafen or pyraziflumid are prominent representatives. For their synthesis, a series of organometallic methods is available, which offer efficient access to a multitude of biphenyl derivatives. The most frequently applied is the Suzuki coupling.

The Suzuki coupling (also called Suzuki-Miyaura coupling or Suzuki reaction or Suzuki-Miyaura reaction) is a cross coupling reaction in which an organoboron compound is reacted with an organic halogenide or sulfonate in the presence of a transition metal catalyst, mostly a Pd or Ni catalyst, and in general also of a base.

Principally, the known processes for preparing nitro- or aminobiphenyls via Suzuki coupling work well, at least on a laboratory scale. However, there is still room for improvement, especially with respect to an application in large-scale industrial processes. For instance, the amount of required Pd in the catalyst is still rather high and minimizing the amount of organic solvents is for economic as well as ecologic reasons desired.

WO 2015/011032 relates to a process for preparing chlorinated biphenylanilines or anilides by Suzuki coupling using a palladium catalyst containing an optionally substituted di-tert-butylphenyl phosphine or a salt thereof as ligand. This catalyst is said to avoid the undesired formation of triphenyl compounds. In the halide starting compound II the leaving group Hal is Br or I. In the examples the coupling reaction is carried out in a mixture of water and 1-butanol as solvent in the presence of potassium carbonate as base. The Pd catalyst is used in an amount of 0.12 mol %, calculated on the basis of the Pd content and relative to 1 mol of the halide.

Although in this process the amount of Pd is already reduced as compared to older processes, there is still room for improvement. Moreover, the use of aromatic bromides or iodides is not desirable, not only because of their cost, especially in case of the iodide, but also because of environmental concerns connected with bromide or iodide containing wastewater.

WO 2018/149813 A1 relates to a process for preparing substituted 2-nitrobiphenyls via Suzuki coupling using a palladium catalyst with specific phosphorus ligands containing at least one aryl substituent and a solvent mixture containing water and an organic solvent which is at least partially miscible with water.

Although in this process the preferred aryl-chlorides are used as coupling partner, still significant amounts (at least 20% by weight in the reaction mixture) of a water miscible organic solvent like tetrahydrofurane is necessary to carry out the reaction. The water soluble organic solvent required for the reaction needs to be separated from the reaction mixture after the reaction, for example by distillation, in order that it do not end up in the waste water, which requires an additional energy consuming step before further product isolation. In RSC Advances, 2011, 1, 1013-1019 is a system presented, which allows the Suzuki coupling of aryl-chlorides in water at low palladium-loadings. The catalyst is palladium immobilized on Agarose. A drawback of this system is that especially the yields in case of the relevant substituted aryl-chloride as para-Nitro-chlorobenzene only gives a moderate yield of 70% of the coupling product.

In Chinese Journal of Chemistry, 2015, 33, 705-710 a surfactant connected palladium-catalyst is used with water as the sole solvent. But also in this case, for the relevant substituted aryl-chloride as para-nitro-chlorobenzene, high catalyst loadings of 0.05 mol % are necessary and also 0.5 equivalents of tetrabutylammoniumbromide as an additive besides $K_2CO_3$. For an economic process, it would be desirable to use a low as possible palladium-loading and also to reduce the number of additives in the system.

In Organometallics 2014, 33, 6544-6549, a Pd-catalyst with N-heterocyclic carbenes as ligands are used for the Suzuki-coupling of aryl-chlorides using water as the sole solvent. But also, relatively high palladium-loadings of 0.1 mol % are necessary for the coupling of nitro-substituted chlorobenzene and the coupling product is only obtained in 31% yield.

In Journal of the American Chemical Society, 2012, 134, 3190-3198, a polymeric imidazole palladium catalyst is used in the Suzuki-coupling of aryl-chlorides in water as the solvent. But in this system, in addition to the necessary base, also at least one equivalent of tetrabutylammoniumfluoride is required, to achieve high yields at low palladium loadings. For an economic process it is necessary to keep the number of additives in the system as low as possible. Preferably only the base would be needed.

It was thus an object of the present invention to provide a process for producing nitro-substituted biphenyls via Suzuki coupling which avoids some of the drawbacks of the prior art processes, especially when these are applied on a large scale. Especially it was the object of the present invention to provide a process for producing substituted biphenyls via Suzuki coupling which requires distinctly lower amounts of palladium, suppresses homocoupling, uses aryl-chlorides, water as solvent and is well-suited for large-scale applications with a simple work-up.

Figure 1:
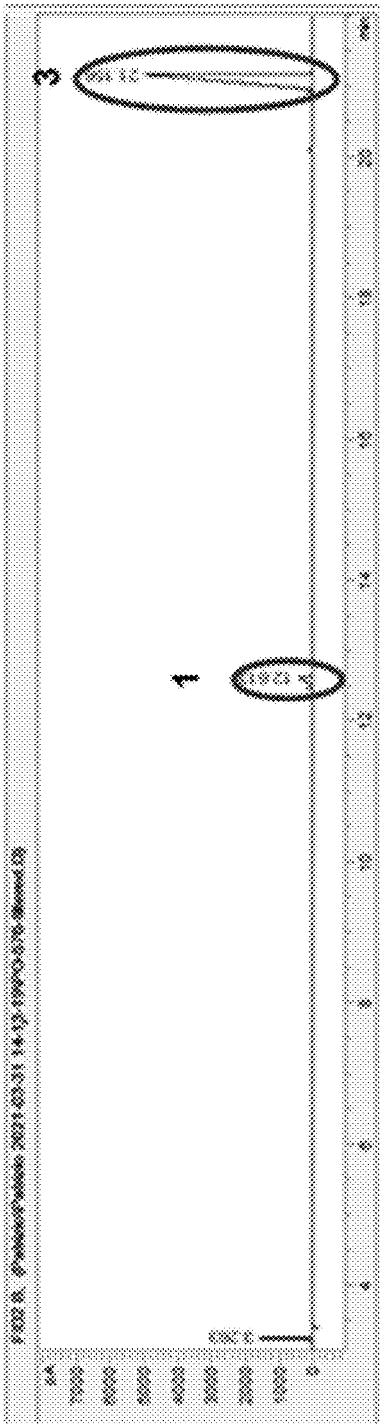
FIG. 1 is a graph showing the yield of (%) of compound 3 over time in a kinetic experiment.

The object is achieved by a process for preparing substituted biphenyls of the formula I

I

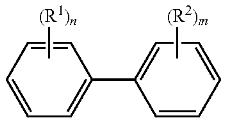

in which the substituents are each defined as follows:

$R^1$ is cyano, nitro, F, Cl, $C_1$-$C_4$-alkyl, $C_1$-$C_4$-haloalkyl, $C_3$-$C_{10}$-cycloalkyl which may carry 1, 2, 3 or 4 $C_1$-$C_4$-alkyl substituents; $C_3$-$C_{10}$-halocycloalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, or $C_1$-$C_6$-haloalkoxycarbonyl;

$R^2$ is cyano, nitro, F, Cl, $C_1$-$C_4$-alkyl, $C_1$-$C_4$-haloalkyl, $C_3$-$C_{10}$-cycloalkyl which may carry 1, 2, 3 or 4 $C_1$-$C_4$-alkyl substituents; $C_3$-$C_{10}$-halocycloalkyl, $C_1$-$C_6$-alkoxy, $C_1$-$C_6$-haloalkoxy, $C_1$-$C_6$-alkylcarbonyl, $C_1$-$C_6$-haloalkylcarbonyl, $C_1$-$C_6$-alkoxycarbonyl, or $C_1$-$C_6$-haloalkoxycarbonyl; and n is 0, 1, 2 or 3, where, in case that n is 2 or 3, the $R^1$ radicals may have identical or different definitions; and m is 0, 1, 2 or 3, where, in case that n is 2 or 3, the $R^2$ radicals may have identical or different definitions which comprises reacting a compound of the formula II

II

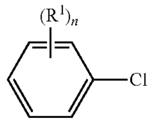

in which $R^1$ and n is as defined above, in the presence of a base and of a palladium catalyst, where the palladium catalyst is introduced into the reaction in the form of a palladium source and a phosphorus ligand of the formula III or a salt thereof

III

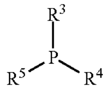

in which $R^3$ is $C_3$-$C_{18}$-alkyl or $C_3$-$C_{10}$-cycloalkyl which is connected to the phosphor atom at a secondary or tertiary carbon atom of the $C_3$-$C_{18}$-alkyl or $C_3$-$C_{10}$-cycloalkyl substituent $R^4$ is $C_1$-$C_{18}$-alkyl or $C_3$-$C_{10}$-cycloalkyl and $R^5$ is $C_1$-$C_{18}$-alkyl or $C_3$-$C_{10}$-cycloalkyl or a palladium complex containing at least one phosphorus ligand of the formula III as defined above or a salt thereof;

with water as the solvent without the use of an additional surfactant or phase transfer catalyst with an organoboron compound of the formula IV

IV

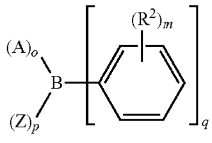

wherein $R^2$ and m are as defined above and the compound of formula IV is selected from the group consisting of (i) boronic acids with o=0, p=2; q=1 and Z=hydroxyl groups, or their trimers;

(ii) boronic acid derivates with o=0, p=2; q=1 and Z=halogen; $C_1$-$C_4$-alkyl, $C_1$-$C_6$-alkoxy or $C_6$-$C_{10}$-aryloxy;

(iii) boronic acids or boronic acid derivatives with o=0, p=1; q=2 and Z=hydroxy, halogen, $C_1$-$C_4$-alkyl, $C_1$-$C_6$-alkoxy or $C_6$-$C_{10}$-aryloxy;

(iv) mixed boronic acids or boronic acid derivatives with o=1, p=1; q=1, A=$C_1$-$C_4$-alkyl and Z=hydroxy, halogen, $C_1$-$C_4$-alkyl, $C_1$-$C_6$-alkoxy or $C_6$-$C_{10}$-aryloxy;

(v) cyclic boronic esters with o=0, p=2 and q=1, wherein the two Z groups form together a bridging group $—O—(CH_2)_r—O—$, wherein r is 2 or 3, so that the two Z groups, together with the boron atom to which they are attached, form a 5- or 6-membered ring, where the $CH_2$ groups are optionally substituted by one or two $C_1$-$C_4$-alkyl groups;

(vi) boronates with o=0, p=3, q=1 and Z=hydroxyl, halogen, $C_1$-$C_4$-alkyl, $C_1$-$C_6$-alkoxy or $C_6$-$C_{10}$-aryloxy, and accompanied by a cation which compensates the negative charge of the boronate anion;

(vii) triarylboranes with o=0, p=0 and q=3;

(viii) tetraarylborates with o=0, p=0 and q=4, and accompanied by a cation which compensates the negative charge of the borate anion;

where the reaction is carried out at a temperature of from 60 to 150° C.

The organic moieties mentioned in the above definitions of the variables are—like the term halogen—collective terms for individual listings of the individual group members.

The term halogen denotes in each case fluorine, bromine, chlorine or iodine, in particular fluorine, chlorine or bromine.

The term "alkyl" as used herein and in the alkyl moieties of alkoxy, alkylcarbonyl, alkoxycarbonyl and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl"), 1 to 6 ("$C_1$-$C_6$-alkyl") or 1 to 8 ("$C_1$-$C_6$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally n-butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl and the isomers thereof.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl") or 1 to 6 ("$C_1$-$C_6$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like.

Examples for $C_1$-$C_4$-haloalkyl are, apart those mentioned for $C_1$-$C_3$-haloalkyl, 4-chlorobutyl and the like.

"Methyl which is substituted by 1, 2 or 3 fluorine atoms" is fluoromethyl, difluoromethyl or trifluoromethyl.

"$C_1$-$C_6$-Hydroxyalkyl" is $C_1$-$C_6$-alkyl, as defined above, where one hydrogen atom is replaced by a hydroxy group. Examples are hydroxymethyl, 1-hydroxyethyl, 2-hydroxyethyl, 1-hydroxypropyl, 2-hydroxypropyl, 3-hydroxypropyl, 1-hydroxy-1-methylethyl, 2-hydroxy-1-methylethyl, 1-hydroxybutyl, 2-hydroxybutyl, 3-hydroxybutyl, 4-hydroxybutyl, 1-hydroxypentyl, 2-hydroxypentyl, 3-hydroxypentyl, 4-hydroxypentyl, 5-hydroxypentyl, 1-hydroxyhexyl, 2-hydroxyhexyl, 3-hydroxyhexyl, 4-hydroxyhexyl, 5-hydroxyhexyl, 6-hydroxyhexyl, and the like.

The term "cycloalkyl" as used herein refers to mono- or bicyclic saturated hydrocarbon radicals having 3 to 10 ("$C_3$-$C_{10}$-cycloalkyl"), 3 to 8 ("$C_3$-$C_8$-cycloalkyl"), in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms are cyclopropyl and cyclobutyl. Examples of monocyclic radicals having 3 to 5 carbon atoms are cyclopropyl, cyclobutyl and cyclopentyl. Examples of monocyclic radicals having 3 to 6 carbon atoms are cyclopropyl, cyclobutyl, cyclopentyl and cyclohexyl. Examples of monocyclic radicals having 3 to 8 carbon atoms are cyclopropyl, cyclobutyl, cyclopentyl, cyclohexyl, cycloheptyl and cyclooctyl. Examples of monocyclic radicals having 3 to 10 carbon atoms are cyclopropyl, cyclobutyl, cyclopentyl, cyclohexyl, cycloheptyl, cyclooctyl, cyclononyl and cyclodecyl. The bicyclic radicals can be condensed or bridged rings. Examples of bicyclic condensed radicals having 6 to 10 carbon atoms comprise bicyclo[3.1.0]hexyl, bicyclo[3.2.0]heptyl, bicyclo[3.3.0]octyl (1,2,3,3a,4,5,6,6a-octahydropentalenyl), bicyclo[4.2.0]octyl, bicyclo[4.3.0]nonyl (2,3,3a,4,5,6,7,7a-octahydro-1H-indene), bicyclo[4.4.0]decyl (decalinyl) and the like. Examples of bridged bicyclic condensed radicals having 7 to 10 carbon atoms comprise bicyclo[2.2.1]heptyl, bicyclo[3.1.1]heptyl, bicyclo[2.2.2]octyl, bicyclo[3.2.1]octyl and the like. Preferably, the term cycloalkyl denotes a monocyclic saturated hydrocarbon radical.

The term "halocycloalkyl" as used herein, which is also expressed as "cycloalkyl which is partially or fully halogenated", refers to mono- or bicyclic saturated hydrocarbon groups having 3 to 10 ("$C_3$-$C_{10}$-halocycloalkyl") or 3 to 8 ("$C_3$-$C_4$-halocycloalkyl") or preferably 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

"Alkoxy" is an alkyl group attached via an oxygen atom. The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom.

The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is 5 additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

"Haloalkoxy" is a haloalkyl group attached via an oxygen atom. The term "$C_1$-$C_2$-haloalkoxy" is a $C_1$-$C_2$-haloalkyl group, as defined above, attached via an oxygen atom.

The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$-$C_2F_5$, $OCF_2$-$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "alkylcarbonyl" is a $C_1$-$C_6$-alkyl ("$C_1$-$C_6$-alkylcarbonyl"), preferably a $C_1$-$C_4$-alkyl ("$C_1$-$C_4$-alkylcarbonyl") group, as defined above, attached via a carbonyl [C(=O)] group. Examples are acetyl (methylcarbonyl), propionyl (ethylcarbonyl), propylcarbonyl, isopropylcarbonyl, n-butylcarbonyl and the like.

The term "haloalkylcarbonyl" is a $C_1$-$C_6$-haloalkyl ("$C_1$-$C_6$-haloalkylcarbonyl"), preferably a $C_1$-$C_4$-haloalkyl ("$C_1$-$C_4$-haloalkylcarbonyl") group, as defined above, attached via a carbonyl [C(=O)] group. Examples are trifluoromethylcarbonyl, 2,2,2-trifluoroethylcarbonyl and the like.

The term "alkoxycarbonyl" is a $C_1$-$C_6$-alkoxy ("$C_1$-$C_6$-alkoxycarbonyl"), preferably a $C_1$-$C_4$-alkoxy ("$C_1$-$C_4$-alkoxycarbonyl") group, as defined above, attached via a carbonyl [C(=O)] group. Examples are methoxycarbonyl, ethoxycarbonyl, propoxycarbonyl, isopropoxycarbonyl, n-butoxycarbonyl and the like.

The term "haloalkoxycarbonyl" is a $C_1$-$C_6$-haloalkoxy ("$C_1$-$C_6$-haloalkoxycarbonyl"), preferably a $C_1$-$C_4$-haloalkoxy ("$C_1$-$C_4$-haloalkoxycarbonyl") group, as defined above, attached via a carbonyl [C(=O)] group. Examples are trifluoromethoxycarbonyl, 2,2,2-trifluoroethoxycarbonyl and the like.

If the term "aryl" as used herein and in the aryl moieties of aryloxy is used without prefix ($C_n$-$C_m$), it indicates an aryl group with 6 to 30, in particular 6 to 14, specifically 6 to 10 carbon atoms as ring members. Aryl is a mono-, bi- or polycyclic carbocyclic (i.e. without heteroatoms as ring members) aromatic radical. One example for a monocyclic aromatic radical is phenyl. In bicyclic aryl rings two aromatic rings are condensed, i.e. they share two vicinal C atoms as ring members. One example for a bicyclic aromatic radical is naphthyl. In polycyclic aryl rings, three or more rings are condensed. Examples for polycyclic aryl radicals are phenanthrenyl, anthracenyl, tetracenyl, 1-H-benzo[a] phenalenyl, pyrenyl and the like.

"$C_6$-$C_{10}$-Aryl" is phenyl, 1-naphthyl or 2-naphthyl.

"Aryloxy" is aryl, as defined above, bound via an oxygen atom to the remainder of the molecule. "$C_6$-$C_{10}$-Aryloxy" is phenoxy, 1-naphthyloxy or 2-naphthyloxy. 5- or 6-membered heteroaryl rings containing 1,2, 3 or 4 heteroatoms selected from the group consisting of N and O as ring members are monocyclic heteroaromatic rings. In the 6-membered heteroaryl rings the heteroatom ring members can only be nitrogen atoms. Examples for 5- or 6-membered heteroaromatic rings containing 1,2,3 or 4 heteroatoms selected from N and O as ring members are 2-furyl, 3-furyl, 1-pyrrolyl, 2-pyrrolyl, 3-pyrrolyl, 1-pyrazolyl, 3-pyrazolyl, 4-pyrazolyl, 5-pyrazolyl, 1-imidazolyl, 2-imidazolyl, 4-imidazolyl, 5-imidazolyl, 2-oxazolyl, 4-oxazolyl, 5-oxazolyl, 3-isoxazolyl, 4-isoxazolyl, 5-isoxazolyl, 1,3,4-triazol-1-yl, 1,3,4-triazol-2-yl, 1,3,4-triazol-3-yl, 1,2,3-triazol-1-yl, 1,2,3-triazol-2-yl, 1,2,3-triazol-4-yl, 1,2,5-oxadiazol-3-yl, 1,2,3-oxadiazol-4-yl, 1,2,3-oxadiazol-5-yl, 1,3,4-oxadiazol-2-yl, tetrazol-1-yl, tetrazol-2-yl, tetrazol-5-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,3,4-tetrazin-1-yl, 1,2,3,4-tetrazin-2-yl, 1,2,3,4-tetrazin-5-yl and the like.

The remarks made below regarding preferred embodiments of the process according to the invention, especially regarding preferred embodiments of the radicals of the different reactants and products (to be more precise preferred embodiments of the variables of the compounds of formulae I, II, III, IV, V and VI, especially with respect to their substituents $R^1$, $R^2$, $R^3$, $R^4$, $R^5$, Ar and n) and of the reaction conditions of the processes according to the invention, apply either taken alone or, more particularly, in any conceivable combination with one another.

The remarks to preferred embodiments of $R^1$ apply both to formula I as well as to formula II, V and VI, unless explicitly specified otherwise. The remarks to preferred embodiments of $R^2$ and n apply both to formula I as well as to formula IV, V and VI, unless explicitly specified otherwise.

In a particular embodiment, the biphenyl compound I is 4-chloro-2'-nitro-biphenyl, 3,4-dichloro-2'-nitro-biphenyl, 3,4-difluoro-2'-nitro-biphenyl, 3,4,5-trifluoro-2'-nitro-biphenyl, 3-chloro-4,5-difluoro-2'-nitro-biphenyl, 3,4-dichloro-5'-fluoro-2'-nitro-biphenyl or 3,5-dichloro-4-fluoro-2'-nitrobiphenyl. Specifically, the biphenyl compound I is 4-chloro-2'-nitro-biphenyl, 3,4-dichloro-2'-nitro-biphenyl, 3,4,5-trifluoro-2'-nitro-biphenyl or 3,4-dichloro-5'-fluoro-2'-nitro-biphenyl; very specifically 4-chloro-2'-nitro-biphenyl or 3,4,5-trifluoro-2'-nitro-biphenyl.

The organoboron compound IV as defined under (i) in which o=0, p=2; q=1 and Z=OH is a boronic acid of formula IVa. Its trimer is a boroxine and has formula tri-IVa:

IVa

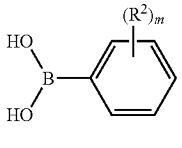

-continued tri-IVa

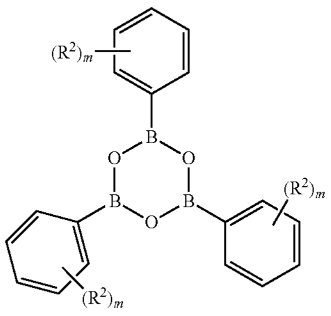

The boronic acid derivates as defined under (ii) with o=0, p=2; q=1 and Z=halogen; $C_1$-$C_4$-alkyl, $C_1$-$C_6$-alkoxy or $C_6$-$C_{10}$-aryloxy are compounds of formula IVb, wherein Z=halogen; $C_1$-$C_4$-alkyl, $C_1$-$C_6$-alkoxy or $C_6$-$C_{10}$-aryloxy:

IVb

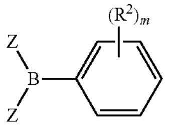

The boronic acids or boronic acid derivatives as defined under (iii) with o=0, p=1; q=2 and Z=hydroxy, halogen, $C_1$-$C_4$-alkyl, $C_1$-$C_6$-alkoxy or $C_6$-$C_{10}$-aryloxy are compounds of formula IVc (boronic acids) or compounds of formula IVd (boronic acid derivatives), wherein Z=halogen, $C_1$-$C_4$-alkyl, $C_1$-$C_6$-alkoxy or $C_6$-$C_{10}$aryloxy:

IVc

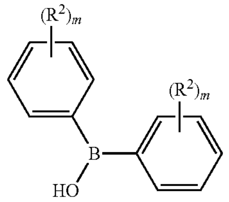

IVd

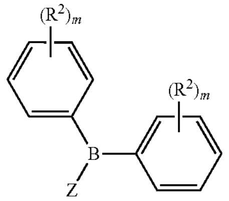

The mixed borinic acids or borinic acid derivatives as defined under (iv) with o=1, p=1; q=1, A=$C_1$-$C_4$-alkyl and Z=hydroxy, halogen, $C_1$-$C_4$-alkyl, $C_1$-$C_6$-alkoxy or $C_6$-$C_{10}$-aryloxy are compounds of formula IVe (mixed borinic acids) or compounds of formula IVf (mixed boronic acid derivatives), wherein Z=halogen, $C_1$-$C_4$-alkyl, $C_1$-$C_6$-alkoxy or $C_6$-$C_{10}$-aryloxy:

IVe

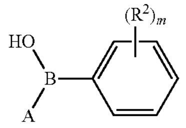

IVf

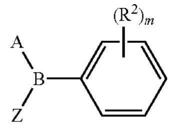

The cyclic boronic esters as defined under (v) with o=0, p=2 and q=1, wherein the two Z groups form together a bridging group —O—$(CH_2)_r$—O—, wherein r is 2 or 3, so that the two Z groups, together with the boron atom to which they are attached, form a 5- or 6-membered ring, where the $CH_2$ groups are optionally substituted by one or two $C_1$-$C_4$-alkyl groups are compounds of formula IVg:

IVg

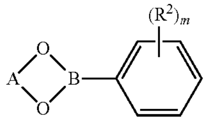

wherein A is —$C(R^{A1})(R^{A2})$—$C(R^{A3})(R^{A4})$— or —$C(R^{A1})(R^{A2})$—$C(R^{A3})(R^{A4})$—$C(R^{A5})(R^{A6})$—, where $R^{A1}$, $R^{A2}$, $R^{A3}$, $R^{A4}$, $R^{A5}$ and $R^{A6}$, independently of each other, are hydrogen or $C_1$-$C_4$-alkyl.

The boronates as defined under (vi) with o=0, p=3, q=1 and Z=hydroxyl, halogen, $C_1$-$C_4$-alkyl, $C_1$-$C_6$-alkoxy or $C_6$-$C_{10}$-aryloxy, and accompanied by a cation which compensates the negative charge of the boronate anion are compounds of formula IVh, wherein each Z is independently hydroxyl, halogen, $C_1$-$C_4$-alkyl, $C_1$-$C_6$-alkoxy or $C_6$-$C_{10}$-aryloxy and $(M^{a+})$i/a is a cation equivalent:

IVh

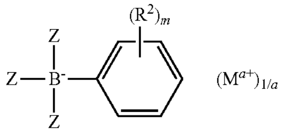

The triarylboranes as defined under (vii) with o=0, p=0 and q=3 are compounds of formula IVi:

IVi

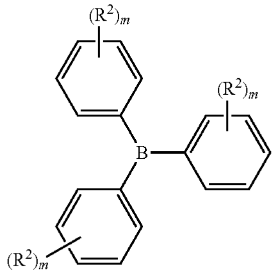

The tetraarylborates as defined under (viii) with o=0, p=0 and q=4, and accompanied by a cation which compensates the negative charge of the borate anion, are compounds of formula IVj, wherein $(M^{a+})_{1/a}$ is a cation equivalent:

IVj

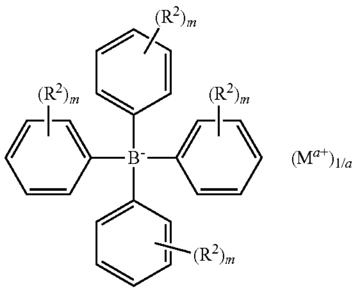

M in compounds IVh and IVj is preferably an alkali or earth alkaline metal cation or an ammonium cation $(NR^aR^bR^cR^d)$+, wherein $R^a$, $R^b$, $R^c$, and $R^d$ independently of each other, are hydrogen, $C_1$-$C_6$-alkyl or $C_1$-$C_6$-hydroxy-alkyl. If M is an alkali metal cation or an ammonium cation, a is 1. If M is an earth alkaline metal cation, a is 2. More preferably, M is an alkali metal cation.

In the above organoboron compounds $R^2$ and m have one of the above general or, in particular, one of the above preferred meanings. In a particular embodiment, $(R^2)_m$ is 4-chloro, 3,4-dichloro, 3,4-difluoro, 3,4,5-trifluoro, 3-chloro-4,5-difluoro or 3,5-dichloro-4-fluoro. Specifically, $(R^2)_m$ is 4-chloro, 3,4-dichloro or 3,4,5-trifluoro. Very specifically, $(R^2)_m$ is 4-chloro or 3,4,5-trifluoro. The positions relate to the 1-position of the attachment of the phenyl ring to the boron atom.

A in the mixed boronic acids or boronic acid derivatives as defined under (iv) is in particular methyl. Preferably, the organoboron compound IV is a phenylboronic acid IVa or a diphenylborinic acid IVc IVa

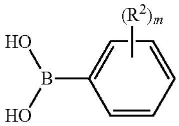

IVc

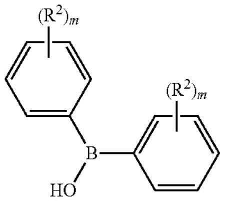

or a mixture of IVa and IVc, in which $R^2$ and n have one of the above general or, in particular, one of the above preferred meanings. In particular, the organoboron compound IV is a phenylboronic acid IVa.

In a particular embodiment, $(R^2)_m$ in IVa and IVc is 4-chloro, 3,4-dichloro, 3,4-difluoro, 3,4,5-trifluoro, 3-chloro-4,5-difluoro or 3,5-dichloro-4-fluoro, more particularly 4-chloro, 3,4-dichloro or 3,4,5-trifluoro, and specifically 4-chloro or 3,4,5-trifluoro. The positions relate to the 1-position of the attachment point of the phenyl ring to the boron atom.

The organoboron compounds as defined under (i) to (viii) and methods for preparing them are known in the art and described, for example, in WO 2015/011032 and the literature cited therein.

The compounds of formulae II and IV are used in a molar ratio of preferably from 5:1 to 1:5, more preferably from 2:1 to 1:2, even more preferably from 1.5:1 to 1:1.5, in particular from 1.1:1 to 1:1.1, specifically from 1.05:1 to 1:1.05, and very specifically of approximately 1:1. "Approximately" is intended to include deviations from ideal stoichiometry caused, for example, by weight errors. Such errors are in general below 10%, mostly below 5%.

The molar ratios of compounds IV as given above relate to the number of phenyl rings contained in the organoboron molecule IV which can react in the Suzuki reaction. Thus, consequently, the molar ratio of compounds II and IVa, IVb, IVe, IVf, IVg or IVh (having one phenyl ring per organoboron molecule which can react in the Suzuki reaction), the compounds IV here counted as such, is preferably from 5:1 to 1:5, more preferably from 2:1 to 1:2, even more preferably from 1.5:1 to 1:1.5, in particular from 1.1:1 to 1:1.1, specifically from 1.05:1 to 1:1.05, and very specifically of approximately 1:1; the molar ratio of compounds II and IVc or IVd (having two phenyl rings per organoboron molecule which can react in the Suzuki reaction), the compounds IV here counted as such, is preferably from 10:1 to 1:2.5, more preferably 4:1 to 1:1, even more preferably from 3:1 to 1:0.75, in particular from 2.2:1 to 1:0.55, specifically from 2.1:1 to 1:0.53, and very specifically of approximately 2:1; the molar ratio of compounds II and tri-IVa or IVi (having three phenyl rings per organoboron molecule which can react in the Suzuki reaction), the compounds IV here counted as such, is preferably from 15:1 to 1:1.7, more preferably from 6:1 to 1:0.7, even more preferably from 4.5:1 to 1:0.5, in particular from 3.3:1 to 1:0.37, specifically from 3.15:1 to 1:0.35, and very specifically of approximately 3:1; and the molar ratio of compounds II and IVj (having four phenyl rings per organoboron molecule which can react in the Suzuki reaction), the compound IVj here counted as such, is preferably from 20:1 to 1:1.25, more preferably from 8:1 to 1:0.5, even more preferably from 6:1 to 1:0.38, in particular from 4.4:1 to 1:0.28, specifically from 4.2:1 to 1:0.26, and very specifically of approximately 4:1.

As however the removal of the halogen compound II from the reaction mixture after completion of the reaction is sometimes more difficult than the removal of the organoboron compound IV, it may be advantageous to use the organoboron compound IV in at least equimolar amounts, better in slight excess, so that the halogen compound II is reacted more or less completely. In this case, compounds of formulae II and IV (the latter counted as the number of phenyl rings contained in the organoboron molecule IV which can react in the Suzuki reaction) are used in a molar ratio of preferably from 1:1 to 1:1.5, more preferably from 1:1 to 1:1.1, in particular from 1:1 to 1:1.05 and specifically from 1:1.01 to 1:1.05. However, the inverse stoichiometry is also possible; i.e. compound II can also be used in slight excess; meaning that compounds of formulae II and IV (the latter counted as the number of phenyl rings contained in the organoboron molecule IV which can react in the Suzuki reaction) are used in a molar ratio of preferably from 1:1 to 1.5:1, more preferably from 1:1 to 1.1:1, in particular from 10 1:1 to 1.05:1 and specifically from 1.01:1 to 1.05:1.

Phenyl rings contained in compound IV which can react in the Suzuki reaction are those phenyl rings which are directly bound to the boron atom. Thus, phenyl rings contained in Z, if this is aryloxy, are not counted.

In case of compounds IV, "equimolar amounts" and "excess" amounts are of course related to the number of phenyl rings contained in compounds IV which can react in the Suzuki reaction.

In the phosphorus ligands III, $R^3$ is $C_3$-$C_{18}$-alkyl or $C_3$-$C_{10}$-cycloalkyl which is connected to the phosphor atom at a secondary or tertiary carbon atom of the $C_1$-$C_{18}$-alkyl or $C_3$-$C_{10}$-cycloalkyl substituent and is in particular selected from 2-propyl, tert-butyl, adamantly, cyclohexyl or cyclopentyl, $R^4$ and $R^5$ are preferably, independently of each other, $C_1$-$C_{18}$-alkyl or $C_3$-$C_{10}$-cycloalkyl.

Salts of the phosphorus ligands are acid addition salts, these thus having the formula:

(III-salt)

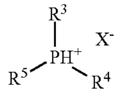

where X— is an anion. Principally any anion derived from a strong acid is suitable, but seeing the desire to avoid certain anions in the waste water, preferred anions are selected from the group consisting of chloride, sulfate, hydrogensulfate, phosphate, hydrogenphosphate, dihydrogenphosphate, perchlorate, tetrafluoroborate, hexafluorophosphate, hydrogenhexafluorozirconate and hydrogenhexafluorotitanate. Specifically, X— is tetrafluoroborate ($BF_4^-$).

The phosphorus ligand Ill is preferably selected from $tBuCy_2P$, $tBu_2CyP$, $tBu_3P$, $Cy_3P$, $Cy_3P$, $AdCy_2P$, $Ad_2nBuP$, $Ad_2CyP$, $Ad_3P$, $Cyp_3P$, $tBu_2CypP$, $tBuCyp_2P$, $tBuiPr_2P$, $tBu_2iPrP$ and $iPr_3P$ (Cy=cyclohexyl, Cyp=cylopentyl, Ad=adamantyl, tBu=tert-Butyl, iPr=iso-propyl)

As said above, the palladium catalyst is introduced into the reaction in the form of a palladium source and a phosphorus ligand of the formula III or a salt thereof, or in form of a palladium complex containing at least one phosphorus ligand of the formula III as defined above or a salt thereof.

If the palladium catalyst is introduced into the reaction in the form of a palladium source and a phosphorus ligand of the formula III or a salt thereof, the complex with the ligand (III) is either formed before the Suzuki reaction starts or, in particular, is formed in situ.

The palladium source is preferably a palladium(II) salt, a palladium(0)- or palladium(I) complex compound, a palladium complex with ligands different from the ligand of formula III or its salt or is metallic palladium which is optionally bound to a carrier.

Suitable Pd(II) salts are for example Pd(II)acetate, Pd(II) benzoate, $PdCl_2$, $Na_2PdCl_4$, $(NH_4)_2PdCl_4$, $PdBr_2$, $PdI_2$, $Pd(NO_3)_2$, $PdSO_4$, $Pd(CF_3COO)_2$, $Pd(tBuCOO)_2$. Preference is given to Pd(II) acetate and $PdCl_2$— In particular, Pd(II) acetate is used.

Suitable palladium(0) or palladium(II) complex compounds are di-μ-iodobis(tritertbutylphosphino)dipalladium (I), di-μ-bromobis(tri-tertbutylphosphino)dipalladium(I) bis (dibenzylideneacetone)palladium(0), tris(dibenzylideneacetone)di-palladium(0), bis(tritertbutylphosphine)palladium(0), bis(tricyclohexylphosphine)palladium(0), bis(triotolylphosphine)palladium(0), tetrakis(triphenylphosphine) palladium(0)

Suitable Pd(II) complexes with ligands different from the ligand of formula III or its salt are for example Pd(II) acetylacetonate, bis(2,2,6,6-tetramethyl-3,5-heptanedionateo)palladium(II), palladium(II)hexafluoracetylacetonate, allyl(cyclopentadienyl)palladium(II), bis(acetonitrile)palladium(ii)(p-toluenesulfonate), allylpalladium(II)chloride dimer, bis(2-methylallyl)palladium(II) chloride dimer, trans-bis(dicyclohexylamine)bis(acetate)palladium(II), chloromethyl(1,5-cyclooctadiene)palladium(II), dichloro(1,5-cyclooctadiene)palladium(II), dibromo(1,5-cyclooctadiene) palladium(II), dichloro(norbonadiene)palladium(II), diacetatebis(triphenylphosphine)palladium(II), dibromo-bis (triphenylphosphine)palladium(II), dichlorobis(triphenylphosphine)palladium(II) diacetate(1,10-phenanthroline) palladium(II), transdichlorodiammine palladium(II), cis-dichloro(N,N,N', N'-tetramethylenediamine)palladium(II), bisbenzonitrile Pd(II) chloride or bisacetonitrile Pd(II) chloride.

A suitable carrier for metallic palladium is charcoal.

The palladium complex containing at least one phosphorus ligand of the formula III as defined above or a salt thereof can be a pre-formed complex of palladium(0) and the ligand Ill or a salt thereof, or can be a pre-formed palladium(II)-, palladium(I) or palladium(0) complex and the ligand Ill or a salt thereof.

In case that a Pd(II) salt or a Pd(II) complex or a Pd(I) complex is used, Pd(II) is reduced to Pd(0) before the Suzuki reaction starts. The reduction generally takes place in situ.

In one preferred embodiment, the palladium catalyst is introduced into the reaction in form of a palladium(II) salt, specifically Pd(II) acetate or $PdCl_2$, and the 5 ligand III or a salt thereof.

In another preferred embodiment, the palladium catalyst is introduced into the reaction in form of a pre-formed complex of palladium(0) or (II) and the ligand III or a salt thereof.

If the palladium catalyst is not introduced into the reaction in form of the preformed complex of palladium and the ligand III, but in form of a Pd source (e.g. a palladium(II) salt, a palladium complex with ligands different from III (or its salt) or a palladium(0) source), and a phosphorus ligand of the formula III or a salt thereof, the Pd source (calculated on the basis of the Pd content) and the ligand of formula III or its salt are used in a molar ratio of preferably from 5:1 to 1:5, more preferably from 2:1 to 1:3, even more preferably from 1.5:1 to 1:2.5, in particular from 1.1:1 to 1:2.5, specifically from 1.05:1 to 1:2.2, very specifically from 1:1 to 1:2.

The Pd catalyst, i.e. the Pd source or the preformed Pd complex containing at least one phosphorus ligand of the formula III as defined above or a salt thereof (in both cases calculated on the basis of the Pd content) can principally be used in an amount of up to 5 mol %, e.g. of from 0.00001 mol % to 5 mol %, relative to 1 mol of compound II or of compound IV (1 mol of compound II or of compound IV corresponding to 100 mol %). If compounds II and IV are not used in equimolar amounts, the above mol % relate to 1 mol of that compound II or IV which is not used in excess. The ligand Ill or its salt and the other reaction conditions allow however for the use of Pd in significantly lower amounts. Thus, preferably, the Pd catalyst (calculated on the basis of the Pd content) is used in an amount of from 0.00001 mol % to 0.5 mol %, more preferably from 0.00001 mol % to 0.01 mol %, in particular from 0.0001 mol % to 0.001 mol %, and specifically from 0.001 mol % to 0.01 mol %.

If compounds II and IV are not used in equimolar amounts, the above mol % relate to 1 mol of that compound II or IV which is not used in excess. Where the amount of the Pd catalyst is related to the compound IV, the latter is of course counted as the number of phenyl rings contained therein which can react in the Suzuki reaction. In other words, where the amount of the Pd catalyst is related to the compound IV, the amount of the Pd catalyst of course actually relates to 1 mol of phenyl rings contained in compound IV which can react in the Suzuki reaction. Thus, for example, in case of boronic acids IVc, which have two phenyl rings, x mol % Pd, relative to 1 mol of compound IVc, means in this case x mol % Pd relative to 1 mol of phenyl rings contained in IVc, and thus to 0.5 mol of compound IVc taken as such. Phenyl rings contained in compound IV which can react in the Suzuki reaction are those phenyl rings which are directly bound to the boron atom. In case of compounds IV, "equimolar amounts" and "excess" amounts are of course related to the number of phenyl rings contained in compounds IV which can react in the Suzuki reaction.

The reaction is carried out in water as the main solvent, preferably the content of water in the total solvent is 95%, more preferably 97% and most preferred 98% by weight. In a preferred embodiment of the invention no other solvent miscible with water is added.

Organic solvents which are only partially or not miscible with water can be present in small amounts, i.e. less than 5%, more preferred less than 3% and most preferred less than 2% of weight of total solvent. These organic solvents are introduced into the reaction mixture usually together with the catalyst and are selected from alkanes, aromatics or esters. These solvents can be linear alkanes as pentane, hexane, heptane, cyclic alkanes as cyclohexane or cyclohexane, or aromatics like benzene, toluene or xylenes or esters as ethyl acetate or butyl acetate.

In the preferred embodiment of the invention, no surfactants or phase transfer catalysts are added to the reaction.

The Suzuki reaction is carried out in the presence of a base. Suitable are both inorganic and organic bases. Suitable inorganic bases are for example from alkali metal carbonates, e.g. $Li_2CO_3$, $Na_2CO_3$, $K_2CO_3$ or $Cs_2CO_3$, earth alkaline metal carbonates, e.g. $MgCO_3$ or $CaCO_3$, alkali metal phosphates, e.g. $Li_3PO_4$, $Na_3PO_4$, $K_3PO_4$ or $Cs_3PO_4$, earth alkaline metal phosphates, e.g. $Mg_3(PO_4)_2$ or $Ca_3(PO_4)_2$, alkali metal hydrogenphosphates, e.g. $Li_2HPO_4$, $Na_2HPO_4$, $K_2HPO_4$ or $Cs_2HPO_4$, earth alkaline metal hydrogenphosphates, e.g. $MgHPO_4$ or $CaHPO_4$, alkali metal hydroxides, LiOH, NaOH or KOH, and earth alkaline metal hydroxides, e.g. $Mg(OH)_2$ or $Ca(OH)_2$.

Examples for suitable organic bases are open-chained amines, e.g. trimethylamine, triethylamine, tripropylamine, ethyldiisopropylamine and the like, or basic N-heterocycles, such as morpholine, pyridine, lutidine, DABCO, DBU or DBN. Preference is however given to inorganic bases, such as to the above alkali metal carbonates, earth alkaline metal carbonates, alkali metal phosphates, earth alkaline metal phosphates, alkali metal hydrogenphosphates, earth alkaline metal hydrogenphosphates, alkali metal hydroxides and earth alkaline metal hydroxides.

More preference is given to alkali metal carbonates, alkali metal phosphates and alkali metal hydroxides. Even more preferred are alkali metal carbonates and hydroxides, such as the above-mentioned $Na_2CO_3$, $K_2CO_3$, NaOH or KOH.

In view of corrosive properties of carbonates and hydroxides under certain conditions, it may however be more advantageous to use one of the above-listed phosphates. Thus, in an alternative even more preferred embodiment, alkali metal phosphates, such as the above-mentioned $Na_3PO_4$, $K_3PO_4$ are used.

The base is preferably used in an amount 0.5 to 5 mol per mol of compound II or of compound IV, more preferably from 1 to 4 mol per mol of compound II or of compound IV, in particular from 1 to 3 mol per mol of compound II or of compound IV, specifically from 1 to 2.2 mol per mol of compound II or of compound IV, and very specifically from 1 to 2 mol per mol of compound II or of compound IV. If compounds II and IV are not used in equimolar amounts, the above relation is to 1 mol of that compound II or IV which is not used in excess. Where the amount of the base is related to the compound IV, the latter is of course counted as the number of phenyl rings contained therein which can react in the Suzuki reaction. In other words, where the amount of the base is related to the compound IV, the amount of the base of course actually relates to 1 mol of phenyl rings contained in compound IV which can react in the Suzuki reaction. Thus, for example, in case of boronic acids IVc, which have two phenyl rings, x mol % of base, relative to 1 mol of compound IVc, means in this case x mol % of base relative to 1 mol of phenyl rings contained in IVc, and thus to 0.5 mol of compound IVc taken as such.

As said above, phenyl rings contained in compound IV which can react in the Suzuki reaction are those phenyl rings which are directly bound to the boron atom. In case of compounds IV, "equimolar amounts" and "excess" amounts are of course related to the number of phenyl rings contained in compounds IV which can react in the Suzuki reaction. The reaction is preferably carried out at a temperature of from 60 to 150° C.; more preferably from 90 to 110° C.

The reaction pressure is principally not critical. As however elevated temperatures are used and in case that the solvents used have a boiling point beneath the desired temperature, the reaction is in this case generally carried out in a closed vessel. This results in an inherent pressure, which is generally in the range of from 1.1 to 10 bar, in particular from 1.5 to 5 bar, specifically from 2 to 4 bar.

The reaction can be carried out by standard proceedings for Suzuki reactions, e.g. by mixing all reagents, inclusive catalyst or catalyst precursor and ligand, base and the solvent mixture, and reacting them at the desired temperature. Alternatively, the reagents can be added gradually, especially in the case of a continuous or semicontinuous process.

The reaction is preferably carried out in an inert atmosphere in order to avoid the presence of oxygen, e.g. under an argon or nitrogen atmosphere.

The reaction is preferably carried out in a pressure vessel, e.g. an autoclave. After completion of the reaction, the reaction mixture is worked up and the compound of the formula I is isolated in a customary manner.

For example, the solvents are removed, for example under reduced pressure. Preferably, however, the work-up is carried out by adding a non-polar extraction solvent to the reaction mixture, to extract the biaryl-product from the aqueous phase and leaving the salt by-products in the aqueous phase.

Non-polar organic solvents in terms of the present invention are those which have a miscibility with water of below 20 g/100 g of water at 20° C. Examples are aliphatic hydrocarbons, such as alkanes, e.g. pentane, hexane, heptane, octane, mixtures thereof and technical mixtures, such as petrol ether; cycloaliphatic hydrocarbons, such as cycloalkanes, e.g. cyclohexane, cycloheptane, or cyclooctane; chlorinated aliphatic hydrocarbons, such as halogenalkanes, e.g. dichloromethane, trichloromethane, tetrachloromethane, dichloroethane or tetrachloroethane, aromatic hydrocarbons, such as benzene, toluene, the xylenes, ethylbenzene, cumene (isopropylbenzene), chlorobenzene, o-dichlorobenzene or nitrobenzene, open-chained, ethers, such as diethylether, dipropylether, methyl-tert-butylether or methylisobutylether, higher alkanols, such as n-butanol or isobutanol or esters as ethylacetate or butylacetate.

The product I is after the extraction in the organic phase mainly formed by the non-polar organic solvent. Moreover, the organic phase also contains the Pd catalyst. To enhance the yield, the aqueous phase can be extracted once or more times with an organic solvent, such as the above listed non-polar organic solvents. If desired, the product I can then be separated from the catalyst and optionally from other undesired components, such as unreacted starting compounds II and/or IV, via customary means. For example, the compound I is crystallized from the organic phase. Alternatively, the solvent is removed from the organic phase, e.g. by distillation, e.g. under vacuum, optionally after drying the organic phase, and the solid matter is taken up in another solvent in which the compound I crystallizes better.

In yet another alternative, the solid matter is submitted to a chromatographic separation.

Further purification of the product I can be effected if desired; for example by extraction, crystallization, distillation or by chromatography.

If desired, the compound I can be left in the aqueous phase without any further work-up and directly be converted into products of value, such as carboxamides of formula V or the isolated and purified compound I can be used to synthesize products of value such as carboxamides of formula V.

V

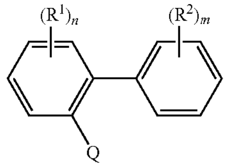

where $R^1$, $R^2$ and n have one of the above general or, in particular, one of the above preferred meanings, and Q is $Q^1$, $Q^2$ or $Q^3$ ($Q^1$)

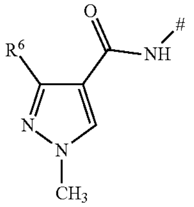

($Q^2$)

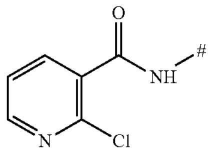

($Q^2$)

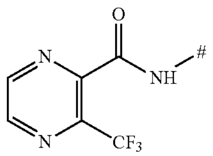

with $R^6$ being methyl, optionally substituted by 1, 2 or 3 fluorine atoms, and # being the attachment point to the remainder of the molecule;

which process comprises (a) preparing a compound of the formula I as defined above with a process as defined above where one $R^1$ is a nitro group;

(b) reducing the nitro group of the compound of formula I obtained in step (a) to an amino group to obtain a compound of the formula VI (VI)

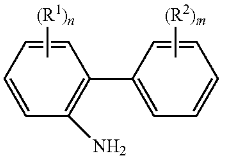

and reacting the amino compound of the formula VI with a compound $Q^{11}$, $Q^{21}$ or $Q^{31}$ ($Q^{11}$)

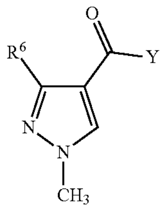

($Q^{21}$)

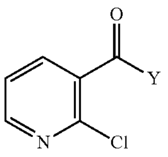

($Q^{31}$)

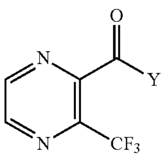

where $R^6$ is as defined above and Y is a leaving group.

Reduction in step (b) may be carried out with hydrogen in the presence of a hydrogenation catalyst, such as Pt on charcoal, or with other reduction agents, such as $SnCl_2$/HCl, Fe/HCl or Fe/$NH_4Cl$.

Reduction can be carried out according to known methods of converting aromatic nitro compounds into the corresponding aromatic amino compounds, such as described, for example, in R. J. Rahaim, R. E. Maleczka (Jr.), Org. Lett., 2005, 7, 5087-10 5090, G. S. Vanier, Synlett, 2007, 131-135, S. Chandrasekhar, S. Y. Prakash, C. L. Rao, J. Org. Chem., 2006, 71, 2196-2199, H. Berthold, T. Schotten, H. Honig, Synthesis, 2002, 1607-1610, and C. Yu, B. Liu, L. Hu, J. Org. Chem., 2001, 66, 919-924.

To obtain compounds V, the amino compound VI is subjected in step (c) to an N-acylation with an acyl precursor $Q^{11}$, $Q^{21}$ or $Q^{31}$.

Suitable leaving groups Y are —OH, a halide, especially chloride or bromide, —$OR^A$, or —O—C(O)—$R^B$.

If compounds $Q^{11}$, $Q^{21}$ or $Q^{31}$ are acids, i.e. Y═OH, the reaction can be performed in the presence of a coupling reagent. Suitable coupling reagents (activators) are well known in the art.

If Y=halide, the reaction is expediently performed in the presence of a base. Suitable bases are those listed above in context with the Suzuki coupling.

If Y═$OR^A$, the compounds $Q^{11}$, $Q^{21}$ or $Q^{31}$ are esters. Suitable esters derive preferably from $C_1$-$C_4$-alkanols $R^AOH$ in which $R^A$ is $C_1$-$C_4$-alkyl, or from $C_2$-$C_6$-polyols such as glycol, glycerol, trimethylolpropane, erythritol, pentaerythritol and sorbitol.

Alternatively, the ester is a so-called active ester, which is obtained in a formal sense by the reaction of the acid $Q^{11}$, $Q^{21}$ or $Q^{31}$ (Y═OH) with an active ester-forming alcohol, such as p-nitrophenol, N-hydroxybenzotriazole (HOBt), N-hydroxysuccinimide or OPfp (pentafluorophenol).

If compounds $Q^{11}$, $Q^{21}$ or $Q^{31}$ are anhydrides, i.e. Y═O—C(O)—$R^B$, these are either a symmetric anhydride or an asymmetric anhydride in which —O—OC—$R^B$ is a group which can be displaced easily by the 2-aminobiphenyl (VI) used in the reaction.

Suitable acid derivatives with which the carboxylic acid $Q^{11}$, $Q^{21}$ or $Q^{31}$ with Y═OH can form suitable mixed anhydrides are, for example, the esters of chloroformic acid, for example isopropyl chloroformate and isobutyl chloroformate, or of chloroacetic acid. The acylation can be carried out under known conditions.

The method of the invention yields compounds I in high yields, although an aromatic chloride is used instead of the generally more reactive aromatic bromides or iodides, as used for example in WO 2015/011032. Moreover, the method requires distinctly lower amounts of Pd than most prior art processes. The Suzuki reaction proceeds very selectively, effectively suppressing homocoupling reactions. The process is very well suited for large scale production, and the workup is very simple. By the choice of ligands according formula III, no water miscible organic solvent is required in the reaction, which makes the work up and isolation of the product even more simple than with the system described in WO 2018/149813. Moreover, as the required amounts of Pd are so low, the catalyst does not need to be recycled, which is a very time-consuming and costly procedure, but can be disposed of after the reaction.

The invention is further illustrated by the following examples.

EXAMPLES

Investigation on the Surfactant Effects

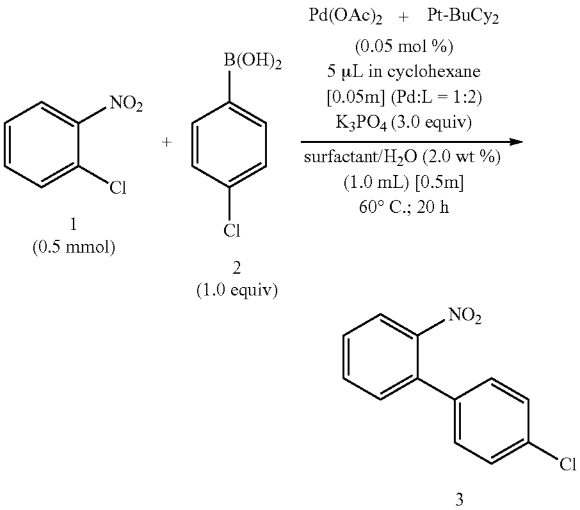

1 (0.5 mmol)

2 (1.0 equiv)

3

| entry | surfactant | conversion [%][b] | yield [%][b] |
|---|---|---|---|
| 1*) | SPGS-550-M | >99 | 93 |
| 2*) | TPGS-750-M | >99 | 95 |
| 3*) | Brij 30 | >99 | 87 |
| 4*) | Brij S100 | >99 | 93 |
| 5*) | IGEPAL CA720 | >99 | 90 |
| 6*) | Sorbitan monopalmitate | >99 | 70 |
| 7*) | Sodium Dodecyl Sulfate | >99 | 89 |
| 8*) | Benzethonium chloride | >99 | 88 |
| 9 | no surfactant | >99 | 97 (93)[c] |

[a] Unless otherwise noted, all reactions were performed in a glovebox with 0.50 mmol of the aryl halide 1, 1.0 equiv of 4-chlorophenylboronic acid 2, $K_3PO_4$ (3.0 equiv) and 10 mL of $Pd(OAc)_2$ + Pt-$BuCy_2$ solution (0.05M in cyclohexane) (0.10 mol %) in 1.0 mL of the respective surfactant in $H_2O$ (2.0 wt %) at 50° C. for 20 h.

[b]Determined by GC analysis after calibration, using mesitylene as internal standard.

[c]Isolated yield.

*)not according to the invention

Screening of Tri-Alkylphosphines at [Pd] Ppm Level Under Optimized Conditions

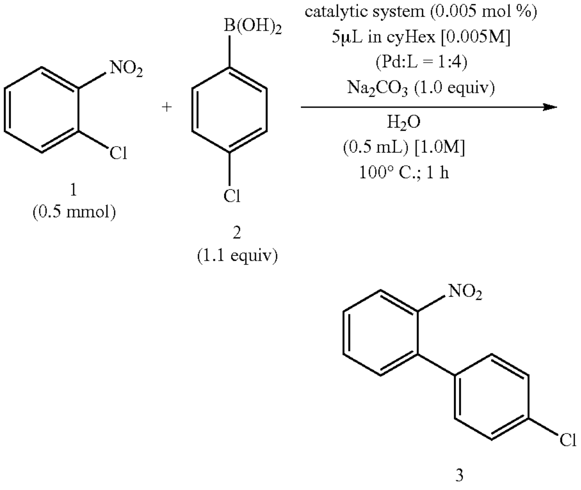

1 (0.5 mmol)

2 (1.1 equiv)

3

| entry | catalytic system | conversion [%][b] | yield [%][b] |
|---|---|---|---|
| 1 | $Pd(OAc)_2$ + $PCy_3$ | 61 | 44[c] |
| 2 | $Pd(OAc)_2$ + $PtBu_3$ | 60 | 45 |
| 3*) | $Pd(OAc)_2$ + $PnBu_3$ | 28 | 5 |
| 4 | $Pd(OAc)_2$ + $PAd_3$ | 78 | 62 |
| 5*) | $Pd(OAc)_2$ + $PMe_3$ | 23 | 8[d] |
| 6*) | $Pd(OAc)_2$ + $PnOct_3$ | 36 | 10 |
| 7 | $Pd(OAc)_2$ + $PAd_2nBu$ | >99 | 88 |
| 8*) | $Pd(OAc)_2$ + $PBn_3$ | 25 | 3[c] |
| 9 | $Pd(OAc)_2$ + $PCp_3$ | 48 | 31 |

[a] Unless otherwise noted, all reactions were performed in a glovebox with 0.5 mmol of the aryl halide 1, 0.55 mmol of the boronic acid 2, 0.5 mmol of $Na_2CO_3$ (1.0 equiv) and 5 μL of the respective catalytic system (Pd:L = 1:4) in cyclohexane (0.005 mol %), in 0.5 mL of $H_2O$ at 100° C. for 1 h.

[b]Determined by GC analysis using mesitylene as internal standard.

[c]In the GC chromatogram is present a peak at 23.77 min.

[d]The stock solution presented solid precipitate.

*)not according to the invention

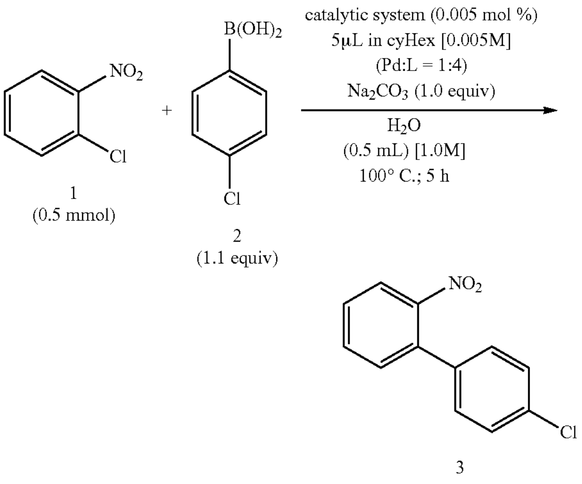

1 (0.5 mmol)

2 (1.1 equiv)

3

| entry | catalytic system | conversion [%][b] | yield [%][b] |
|---|---|---|---|
| 1 | $Pd(OAc)_2$ + $PCy_3$ | 96 | 82 (75)[c] |
| 2 | $Pd(OAc)_2$ + $PtBu_3$ | >99 | 80 (85)[c, d] |
| 3*) | $Pd(OAc)_2$ + $PnBu_3$ | 35 | 13 |
| 4*) | $Pd(OAc)_2$ + $PnOCt_3$ | 39 | 12 |
| 5*) | $Pd(OAc)_2$ + $PMe_3$ | 23 | 2[e] |

[a] Unless otherwise noted, all reactions were performed in a glovebox with 0.5 mmol of the aryl halide 1, 0.55 mmol of the boronic acid 2, 0.5 mmol of $Na_2CO_3$ (1.0 equiv) and 5 mL of the respective catalytic system (Pd:L = 1:4) in cyclohexane (0.005 mol %), in 0.5 mL of $H_2O$ at 100° C. for 5 h.

[b]Determined by GC analysis using mesitylene as internal standard.

[c]Isolated yield.

[d]The isolated product contains also another unknown species.

[e]The stock solution presented a solid precipitate.

*)not according to the invention

Experiments (Entry 1-5) which are not According to the Invention (for Comparison)

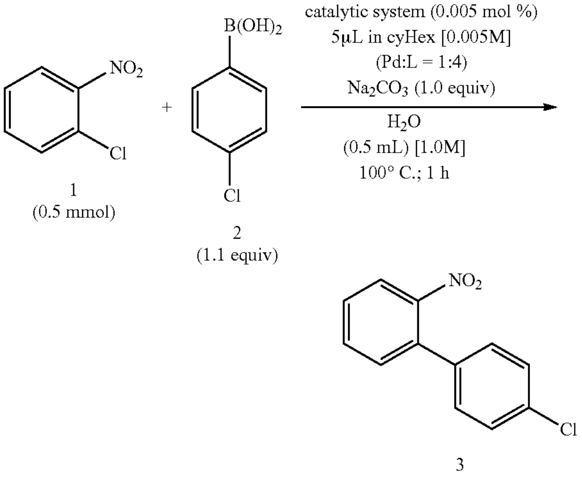

1 (0.5 mmol)

2 (1.1 equiv)

3

| entry | catalytic system | conversion [%][b] | yield [%][b] |
|---|---|---|---|
| 1 | $Pd(OAc)_2$ + $PPh_3$ | 25 | 2 |
| 2 | $Pd(OAc)_2$ + $PPhCy_2$ | 53 | 33 |
| 3[c] | $Pd(OAc)_2$ + $PPhCy_2$ | 53 | 28 |

-continued

| entry | catalytic system | conversion [%][b] | yield [%][b] |
|---|---|---|---|
| 4 | $Pd(OAc)_2$ + $PPh_2Cy$ | 30 | 4 |
| 5 | $Pd(OAc)_2$ + SPhos | 36 | 16 |

[a] Unless otherwise noted, all reactions were performed in a glovebox with 0.5 mmol of the aryl halide 1, 0.55 mmol of the boronic acid 2, 0.5 mmol of $Na_2CO_3$ (1.0 equiv) and 5 mL of the respective catalytic system (Pd:L = 1:4) in cyclohexane (0.005 mol %), in 0.5 mL of $H_2O$ at 100° C. for 5 h.

[b]Determined by GC analysis using mesitylene as internal standard.

[c]The reaction was run for 5 h.

Effect of Different Solvent Using $Na_2CO_3$ as Base with $Pd(OAc)_2$+$PtBuCy_2$ (0.005 Mol %):

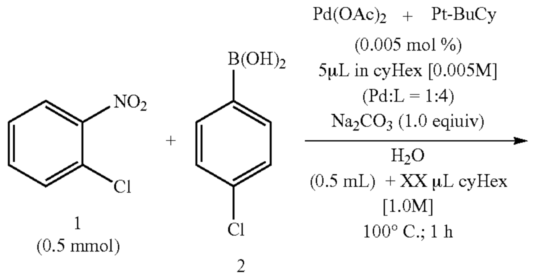

1 (0.5 mmol)

2 (1.1 equiv)

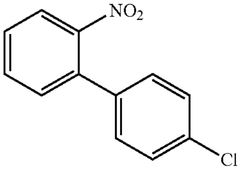

3

| entry | cyHex addition (μL) | conversion [%][b] | yield [%][b] |
|---|---|---|---|
| 1 | none | >99 | 91 |
| 2 | 10 | >99 | 91 |
| 3 | 100 | 87 | 62 |

[a] Unless otherwise noted, all reactions were performed in a glovebox with 0.5 mmol of the aryl halide 1, 0.55 mmol of the boronic acid 2, 0.5 mmol of NaOH (1.0 equiv) and 5 μL of $Pd(OAc)_2$ + $PtBuCy_2$ solution (Pd:L = 1:4) in cyclohexane (0.005 mol %), in 0.5 mL of $H_2O$ at 100° C. for 1 h.

[b]Determined by GC analysis using mesitylene as internal standard.

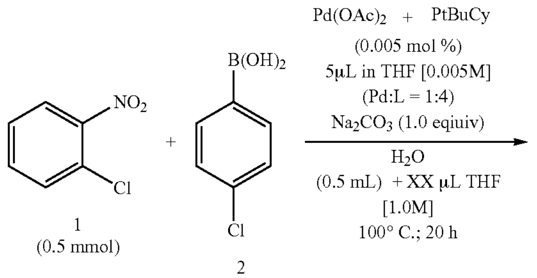

1 (0.5 mmol)

2 (1.1 equiv)

-continued

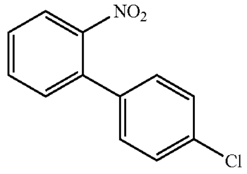

3

| entry | THF addition (μL) | conversion [%][b] | yield [%][b] |
|---|---|---|---|
| 1 | none | >99 | 86 |
| 2 | 10 | >99 | 90 |
| 3 | 100 | >99 | 93 (95)[c] |

[a] Unless otherwise noted, all reactions were performed in a glovebox with 0.5 mmol of the aryl halide 1, 0.55 mmol of the boronic acid 2, 0.5 mmol of NaOH (1.0 equiv) and 5 μL of $Pd(OAc)_2$ + $PtBuCy_2$ solution (Pd:L = 1:4) in tetrahydrofurane (0.005 mol %), in 0.5 mL of $H_2O$ at 100° C. for 20 h.

[b]Determined by GC analysis using mesitylene as internal standard.

[c]Isolated yield.

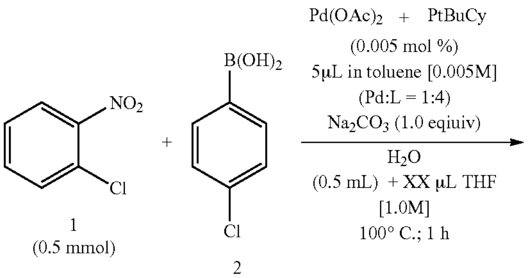

1 (0.5 mmol)

2 (1.1 equiv)

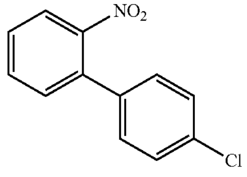

3

| entry | toluene addition (μL) | conversion [%][b] | yield [%][b] |
|---|---|---|---|
| 1 | none | >99 | 89 |
| 2 | 10 | >99 | 90 |
| 3 | 100 | >99 | 93 |

[a] Unless otherwise noted, all reactions were performed in a glovebox with 0.5 mmol of the aryl halide 1, 0.55 mmol of the boronic acid 2, 0.5 mmol of NaOH (1.0 equiv) and 5 μL of $Pd(OAc)_2$ + $PtBuCy_2$ solution (Pd:L = 1:4) in toluene (0.005 mol %), in 0.5 mL of $H_2O$ at 100° C. for 1 h.

[b]Determined by GC analysis using mesitylene as internal standard.

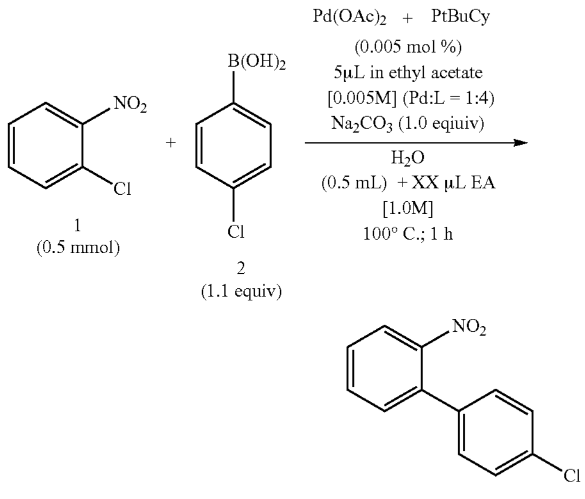

1 (0.5 mmol)

2 (1.1 equiv)

3

| entry | EA addition (μL) | conversion [%][b] | yield [%][b] |
|---|---|---|---|
| 1 | none | >99 | 97 (91)[c] |
| 2 | 10 | >99 | 86 |
| 3 | 100 | >99 | 97 |

[a] Unless otherwise noted, all reactions were performed in a glovebox with 0.5 mmol of the aryl halide 1, 0.55 mmol of the boronic acid 2, 0.5 mmol of NaOH (1.0 equiv) and 5 μL of $Pd(OAc)_2$ + $PtBuCy_2$ solution (Pd:L = 1:4) in ethyl acetate (0.005 mol %), in 0.5 mL of $H_2O$ at 100° C. for 1 h.

[b]Determined by GC analysis using mesitylene as internal standard.

[c]Isolated yield.

Temperature Screening Under Optimized Conditions:

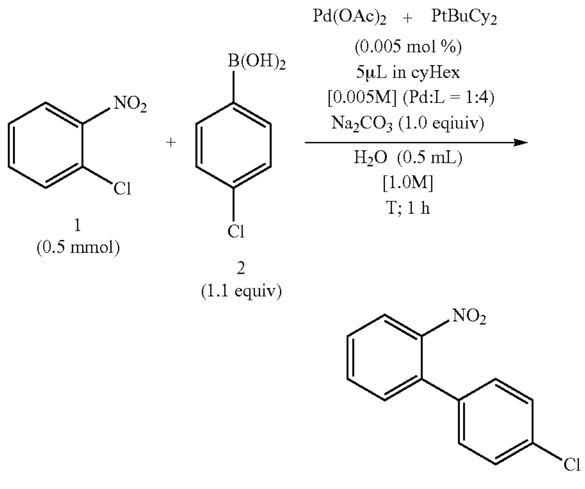

1 (0.5 mmol)

2 (1.1 equiv)

3

-continued

| entry | temperature (° C.) | conversion [%][b] | yield [%][b] |
|---|---|---|---|
| 1 | 80 | >99 | 81 |
| 2 | 90 | >99 | 84 |
| 3 | 120 | >99 | 78 |
| 4 | 140 | >99 | 80[c] |

[a] Unless otherwise noted, all reactions were performed in a glovebox with 0.5 mmol of the aryl halide 1, 0.55 mmol of the boronic acid 2, 0.5 mmol of $Na_2CO_3$ (1.0 equiv) and 5 μL of $Pd(OAc)_2$ + $PtBuCy_2$ (Pd:L = 1:4) in cyclohexane (0.005 mol %), in 0.5 mL of $H_2O$ at the given temperature for 1 h.

[b]Determined by GC analysis using mesitylene as internal standard.

Investigation of Suzuki-Miyaura Cross-Coupling at Lower [Pd] Ppm Level:

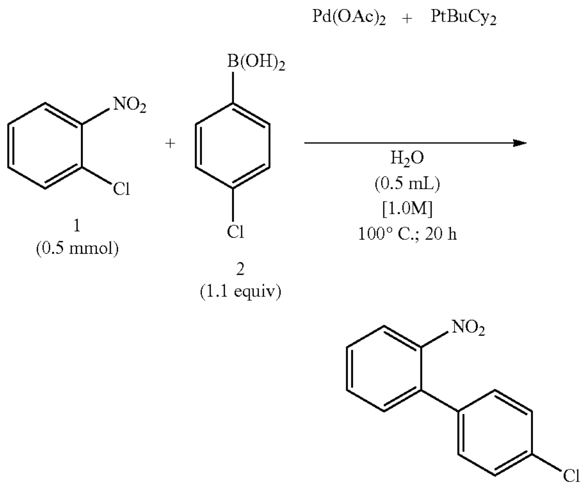

1 (0.5 mmol)

2 (1.1 equiv)

3

| entry | μL of catalyst added | conversion [%][b] | yield [%][b] |
|---|---|---|---|
| 1 | 5 (0.0005 mol %) | 65 | 35 |
| 2 | 10 (0.001 mol %) | 75 | 51 |
| 3 | 25 (0.0025 mol %) | 81 | 67 |

[a] Unless otherwise noted, all reactions were performed in a glovebox with 0.5 mmol of the aryl halide 1, 0.55 mmol of the boronic acid 2, 0.5 mmol of $Na_2CO_3$ (1.0 equiv) and the respective μL of $Pd(OAc)_2$ + $PtBuCy_2$ in cyclohexane (Pd:L = 1:4), in 0.5 mL of $H_2O$ at 100° C. for 20 h.

[b]Determined by GC analysis using mesitylene as internal standard.

Kinetic Experiment on Suzuki-Miyaura Cross Coupling at 50 ppm Catalyst Loading:

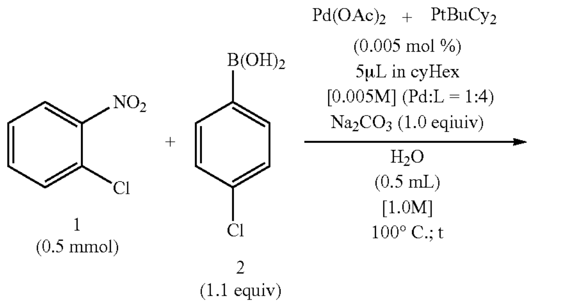

1 (0.5 mmol)

2 (1.1 equiv)

-continued

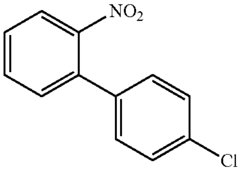

3

NOTE: 5 different reactions were set at the same to. After dedicated time, the respective tube was opened and analyzed by GC using mesitylene as internal standard. After 60 min isolated 103.6 mg of yellow solid (89%). The yield (%) of compound three over time is illustrated in FIG. 1.

Investigation with 1.0 Equiv of Base:

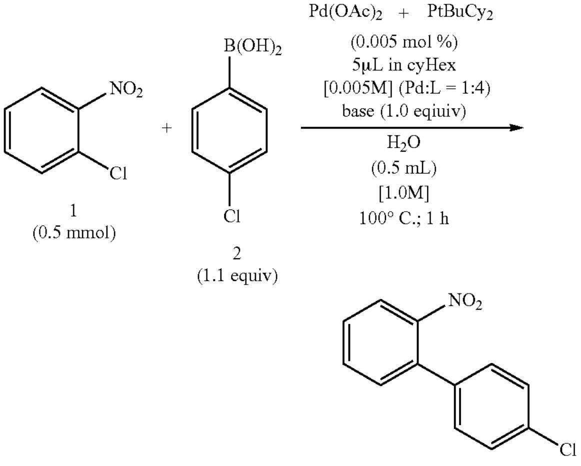

1 (0.5 mmol)

2 (1.1 equiv)

3

| entry | base | conversion [%][b] | yield [%][b] |
|---|---|---|---|
| 1 | $K_3PO_4$ | 89 | 68 |
| 2 | $K_2CO_3$ | >99 | 83 |
| 3 | NaOH | 97 | 81 |
| 4 | KOH | 82 | 64 |

[a] Unless otherwise noted, all reactions were performed in a glovebox with 0.5 mmol of the aryl halide 1, 0.55 mmol of the boronic acid 2, 0.5 mmol of respective base (1.0 equiv) and 5 μL of $Pd(OAc)_2$ + $PtBuCy_2$ (Pd:L = 1:4) in cyclohexane (0.005 mol %), in 0.5 mL of $H_2O$ at 100° C. for 1 h.

[b]Determined by GC analysis using mesitylene as internal standard.

Test Experiment Removing Cyclohexane from the Reaction Mixture:

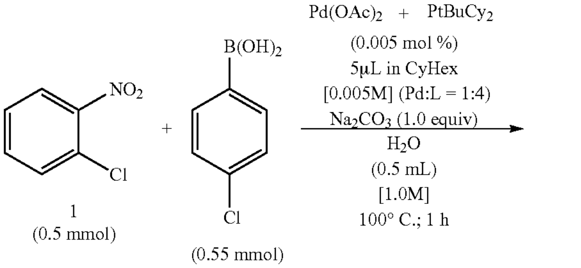

1 (0.5 mmol)

(0.55 mmol)

-continued

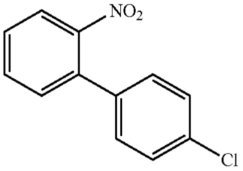

3 full conversion isolated 112,6 mg of yellow oil

[96%]

Note: the pressure tube was transferred outside the glovebox closed with a rubber septum on top. From the Schlenk line it was applied full vacuum for ca. 10 sec. Presumably, the cyclohexane has been removed.

Test Reaction Using a Different Borane Reagent:

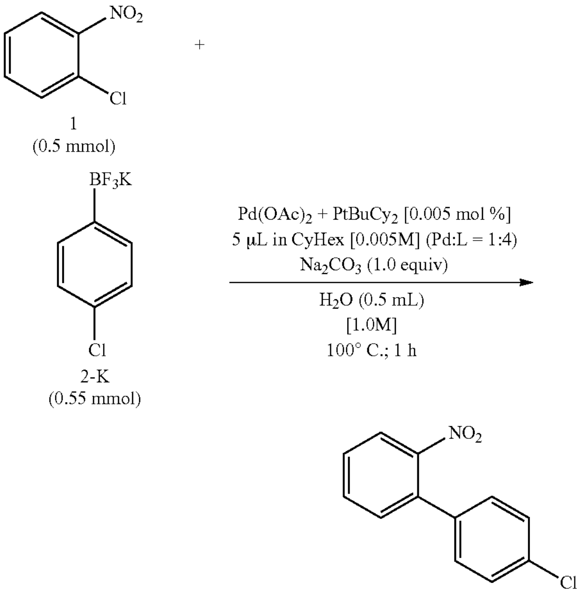

1 (0.5 mmol)

2-K (0.55 mmol)

3 conversion 92% yield 88% isolated 102.6 mg of yellow oil [88%]

GLC analysis

GLC analyses were performed using an AGILENT 6890N equipped with a DB-5 capillary column (30 m x 0.32 mm, 0.25 μm, He carrier gas, 250° C. injection temperature, detector temperature 250° C.; temperature program: start temperature 60° C. for 1 min, heating rate 5° C. · $min^{-1}$ until 120° C. IIIIII, then 15° C. · $min^{-1}$ until 270° C., end temperature 270° C. for 2 min).

$t_r$ = 21.01 min

Test Reaction Using Different Pd Sources:

$[Pd(allyl)Cl]_2$ as Pd(0) catalyst

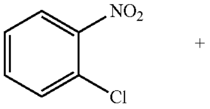

1

(0.5 mmol)

-continued

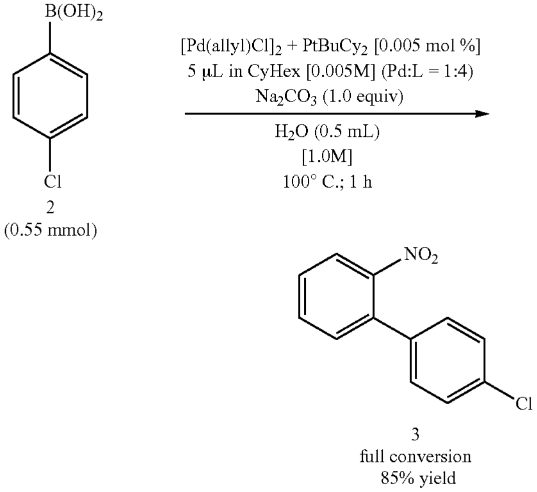

2
(0.55 mmol)
3

General Procedure for Cross-Coupling Reaction

General Procedure for the Preparation of the Catalyst Stock Solutions

In a glovebox, a 10.0 mL vial was charged with 6.0 mg of Pd(OAc)$_2$ (0.25 mmol) and 25.0 mg of Pt-BuCy$_2$ (0.10 mmol, Pd:L=1:4) and diluted in 5.0 mL of the respective solvent, obtaining a 0.005M solution of the catalytic system. The mixture was left stirring in the glovebox and the desired amount (5 μL, 0.002 μmol) was taken with a micropipette and directly injected in the reaction vessel.

General Procedure for Suzuki-Miyaura Cross-Coupling of Aryl Chloride with Aryl Boronic

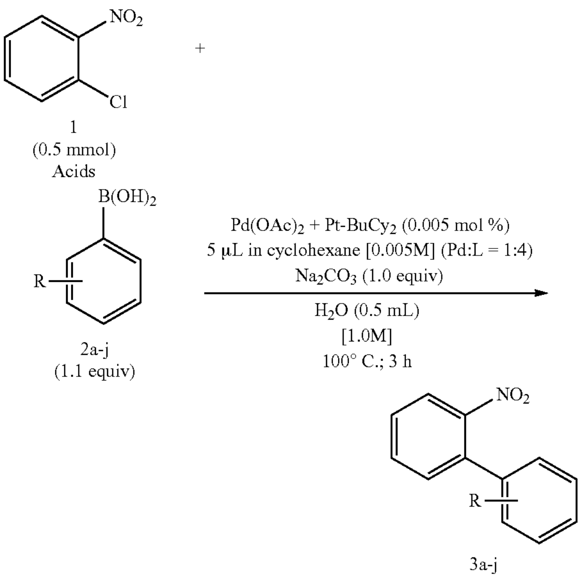

1
(0.5 mmol)
Acids
2a-j
(1.1 equiv)
3a-j

In a glovebox, a 2.0 mL pressure tube was equipped with a magnetic stir bar, 0.55 mmol of the corresponding aryl boronic acid (2a-2j) was added with 0.50 mmol of Na$_2$CO$_3$ (53.0 mg, 1.0 equiv), 5 μL of Pd(OAc)$_2$ and PfBuCy$_2$ solution (0.005M in cyclohexane) (0.002 μmol, 0.005 mol %, Pd:L=1:4) and 0.50 mmol of 1-chloro-2-nitrobenzene (79.0 mg, 1.0 equiv). The tube was sealed and transferred outside the glovebox, where 0.50 mL of H$_2$O were added under a flow of Ar. The tube was finally placed in a preheated 100° C. oil bath for 3 h. After this time, the mixture was diluted with 5.0 mL of brine and extracted with EtOAc (3×2.0 mL). The combined organic phases were dried over MgSO$_4$ and filtered. After concentration under reduce pressure, the crude product was purified by flash column chromatography on silica gel using petrol ether: ethyl acetate=95:5 as eluent to get spectroscopically pure product.

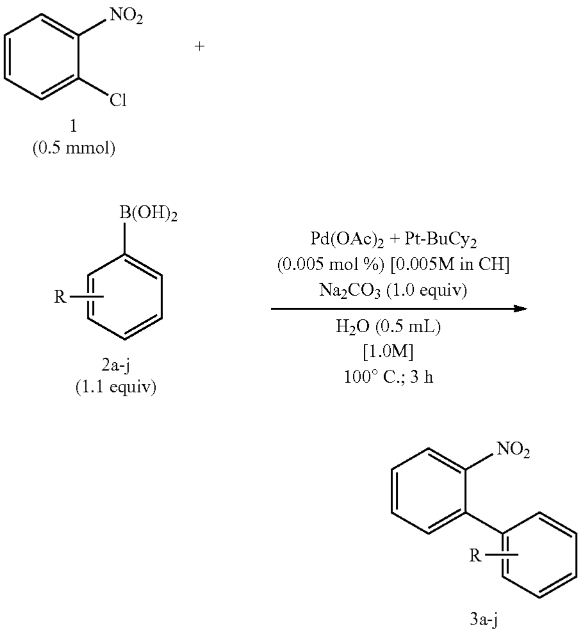

1
(0.5 mmol)
2a-j
(1.1 equiv)
3a-j

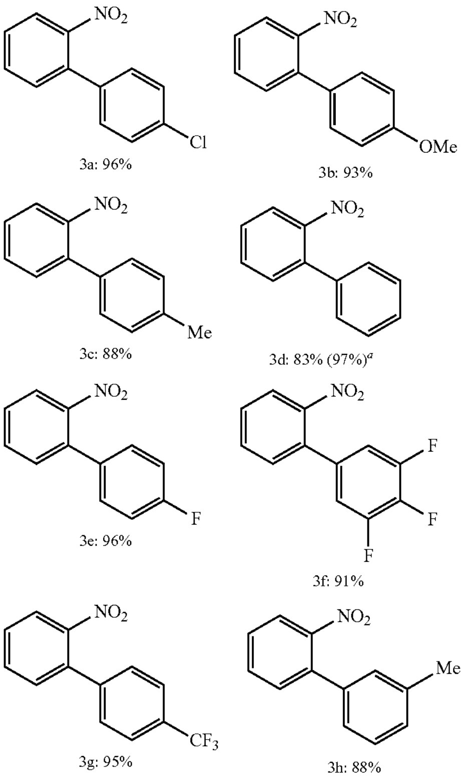
3a: 96%
3b: 93%
3c: 88%
3d: 83% (97%)[a]
3e: 96%
3f: 91%
3g: 95%
3h: 88%

-continued

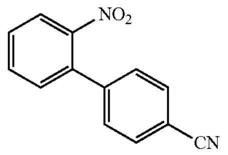

3i: 83%

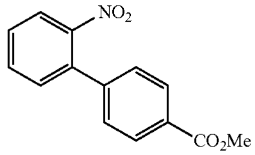

3j: 77%

Unless otherwise noted, all reactions were performed in a glovebox with 0.5 mmol of the aryl chloride 1, 1.1 equiv of the respective boronic acid 2a-j, $Na_2CO_3$ (1.0 equiv) and 5 mL of $Pd(OAc)_2$+Pt-$BuCy_2$ solution in cyclohexane (0.005 mol %) [Pd:L=1:4], in 0.5 mL of $H_2O$ at 100° C. for 3 h. [a] The reaction was set with 10 μL of $Pd(OAc)_2$+Pt-$BuCy_2$ solution in cyclohexane (0.010 mol %) [Pd:L=1:4].

General Procedure for Suzuki-Miyaura Cross-Coupling of Aryl Halides

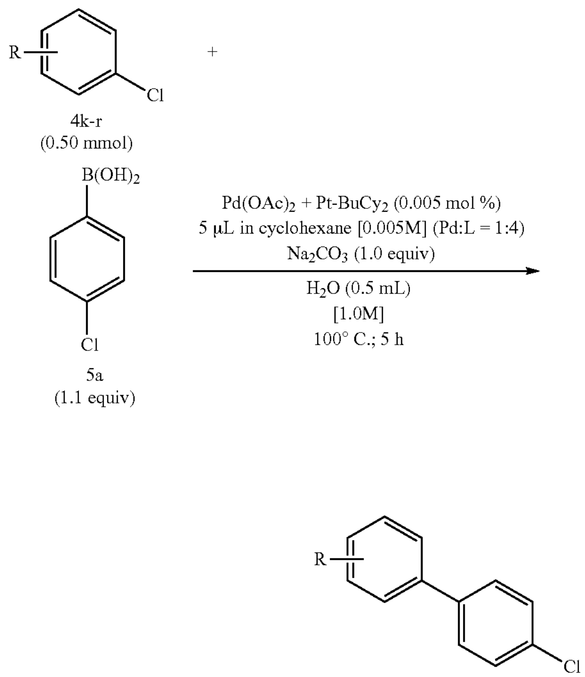

4k-r (0.50 mmol)

5a (1.1 equiv)

6k-r

In a glovebox, a 2.0 mL pressure tube was equipped with a magnetic stir bar, 0.55 mmol of 4-chlorophenylboronic acid (5a) was added with 0.50 mmol of $Na_2CO_3$ (53.0 mg, 1.0 equiv), 5 μL of $Pd(OAc)_2$ and Pt-$BuCy_2$ solution (0.005M in cyclohexane) (0.002 μmol, 0.005 mol %, Pd:L=1:4) and 0.50 mmol of the corresponding aryl chloride (4k-r). The tube was sealed and transferred outside the glovebox, where 0.50 mL of $H_2O$ were added under a flow of Ar. The tube was finally placed in a preheated 100° C. oil bath for 5 h. After this time, the mixture was diluted with 5.0 mL of brine and extracted with EtOAc (3×2.0 mL). The combined organic phases were dried over $MgSO_4$ and filtered. After concentration under reduce pressure, the crude product was purified by flash column chromatography on silica gel using petrol ether:ethyl acetate=95:5 as eluent to get spectroscopically pure product.

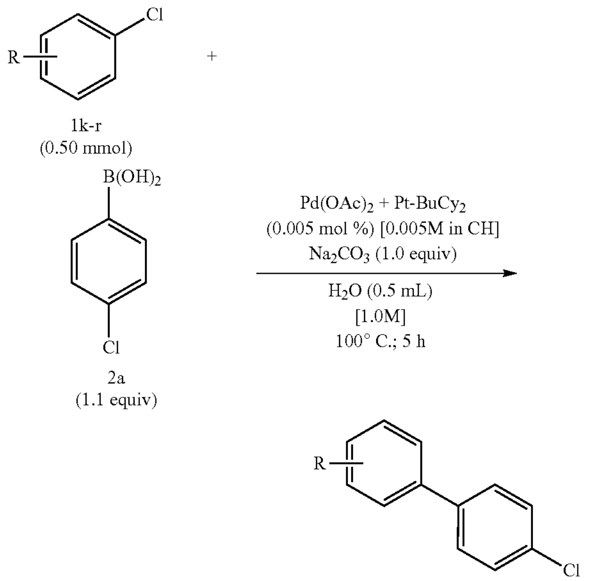

1k-r (0.50 mmol)

2a (1.1 equiv)

3k-r

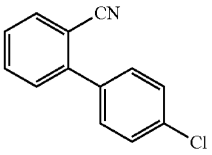

3k: 64%

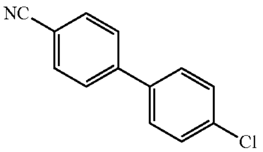

3l: 63%

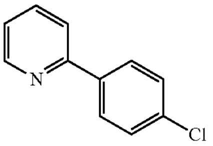

3m: 63%

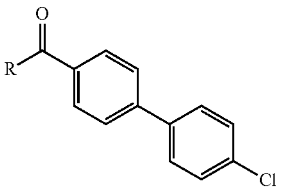

(R = OMe)3n: 55% (82%)[b]
(R = Me) 3o: 65%
(R = H) 3p: 75%
(R = Ph) 3q: 71%

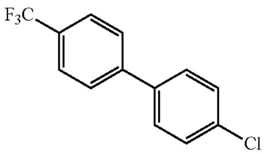

6r: 62%

Unless otherwise noted, all reactions were performed in a glovebox with 0.5 mmol of the respective aryl chloride 1k-r, 1.1 equiv of the boronic acid 2a, $Na_2CO_3$ (1.0 equiv) and 5 mL of $Pd(OAc)_2$+Pt-$BuCy_2$ solution in cyclohexane (0.005 mol %) [Pd:L=1:4], in 0.5 mL of $H_2O$ at 100° C. for 5 h. [a] The reaction was set with 10 μL of $Pd(OAc)_2$+$PtBuCy_2$ solution in cyclohexane (0.010 mol %) [Pd:L=1:4].

Scale-Up Experiments

1. Bixafen Precursor

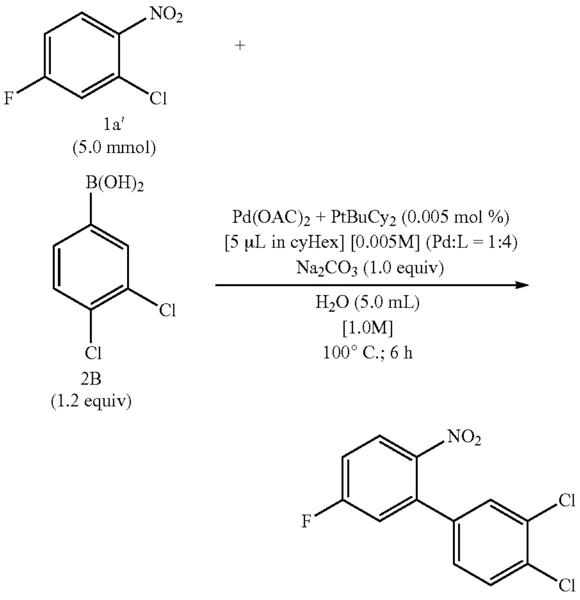

1a' (5.0 mmol)

2B (1.2 equiv)

3B

| | wt | Mw (g/mol) | mmol | eq | V |
|---|---|---|---|---|---|
| 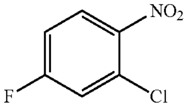 [SMILES: O=[N+]([O-])c1ccc(F)cc1Cl] | 880 mg | 175.54 | 5.0 | 1 | |
| 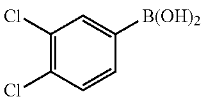 | 1.15 g | 190.82 | 5.5 | 1.1 | — |
| $Na_2CO_3$ | 530 mg | 106 | 5.0 | 1 | |
| $Pd(OAc)_2$ + $PtBuCy_2$ | | | 0.0005 | 0.005 mol % | 50 μL in CH |
| $H_2O$ | 5.0 mL | | | | |

In a glovebox, a 25.0 mL pressure tube equipped with a stirrer bar was charged with 1.15 g of boronic acid 2B (1.2 equiv), 530 mg of $Na_2CO_3$ (1.0 equiv), 50 μL of a 0.005 M solution of $Pd(OAc)_2$+$PtBuCy_2$ (Pd:L=1:4) in cyclohexane and 880 mg of the aryl chloride 1h. The vial was capped and transferred outside the glovebox, where 5.0 ml of $H_2O$ were added under a flow of Ar. The tube was heated at 100° C. for 6 h. After this time, the tube was cooled down to rt and the mixture was diluted with 2.0 mL brine and extracted with EtOAc (3x5.0 mL), the combined organic extracts were dried over $MgSO_4$ and concentrate in vacuo. Subsequently, the final product was recrystallized using 10 mL EtOH to obtain 1.36 g of product 3B as yellow solid (74%). The product was characterized by 1H and 13C NMR, HRMS analysis as well as elemental analysis. The results fit the previously reported data for 3B.

5 g-Experiment Boscalid Precursor

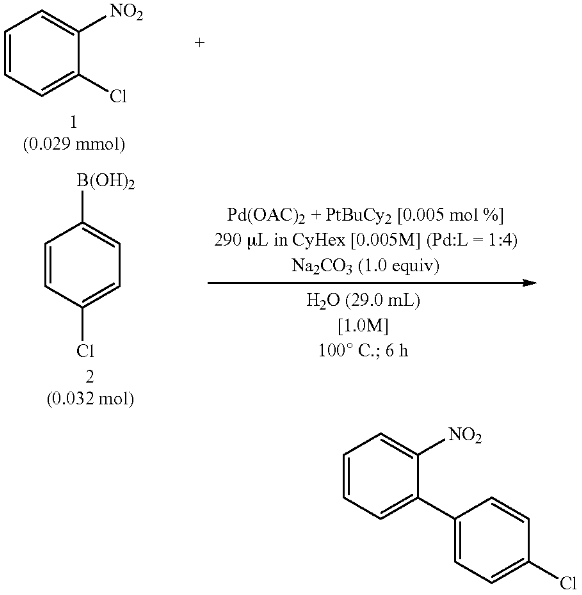

1 (0.029 mmol)

2 (0.032 mol)

3

| | wt | Mw (g/mol) | mmol | eq | V |
|---|---|---|---|---|---|
| 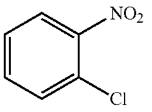 | 4.56 g | 157.55 | 29 | 1 | |
| 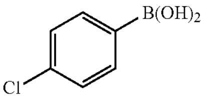 | 5.0 g | 156.37 | 32 | 1.1 | — |
| $Na_2CO_3$ | 3.4 g | 106 | 29 | 1 | |
| $Pd(OAc)_2$ + $PtBuCy_2$ | | | 0.0005 | 0.005 mol % | 290 μL in CyHex |
| $H_2O$ | 29.0 mL | | | | |

In a glovebox, a glass autoclave equipped with a spherical stirrer bar was charged with 5.0 g of boronic acid 2 (1.1 equiv), 3.4 g of $Na_2CO_3$ (1.0 equiv) and 290 μL of a 0.005 M solution of $Pd(OAc)_2$+$PtBuCy_2$ (Pd:L=1:4) in cyclohexane and 4.56 g of the aryl chloride 1. The autoclave was screwed inside the glovebox and transferred outside, where 29.0 mL of $H_2O$ were added under a flow of Ar. The glass autoclave was finally heated in an oil bath at 100° C. for 6 h. After this time the mixture was diluted with 10.0 mL of brine and subsequently extracted with EtOAc (2x5.0 mL) and the combined organic phases were dried over $MgSO_4$, filtered and then analyzed by GC. Subsequently, the final product was recrystallized using 10 mL EtOH to obtain 5.477 g of product 3 as yellow solid (81%). The product was characterized by 1H and 13C NMR, HRMS analysis as well as elemental analysis. The results fit the previously reported data for 3.

Figure 2:
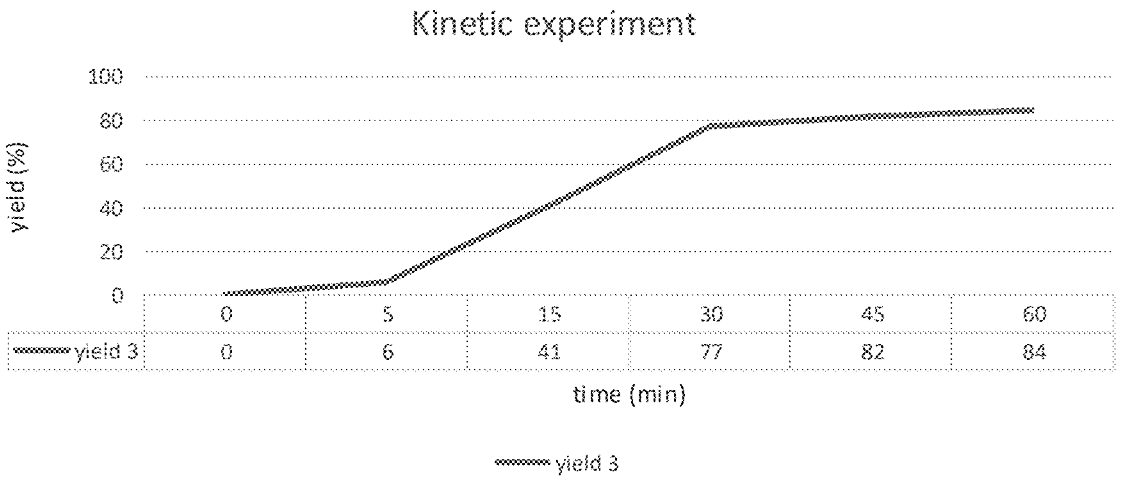
FIG. 2 is a GC analysis of the crude reaction mixture from a Boscalid precursor experiment.

FIG. 2 is a GC analysis of the crude reaction mixture 1. 50 g-Experiment Boscalid Precursor

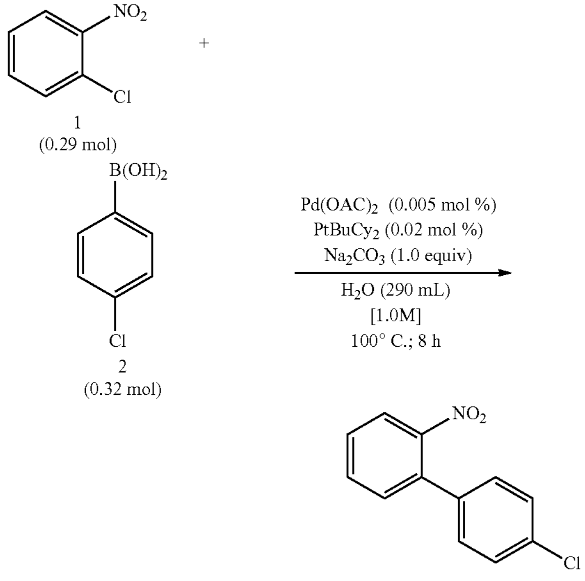

1 (0.29 mol)

2 (0.32 mol)

3

| | wt | Mw (g/mol) | mmol | eq | V |
|---|---|---|---|---|---|
| 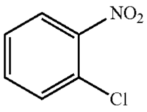 | 46 g | 157.55 | 290 | 1 | |

-continued

| | wt | Mw (g/mol) | mmol | eq | V |
|---|---|---|---|---|---|
| 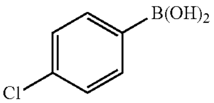 | 50 g | 156.37 | 320 | 1.1 | — |
| $Na_2CO_3$ | 30.7 g | 106 | 290 | 1 | |
| $Pd(OAc)_2$ | 4.0 mg | 224.51 | $1.78 \cdot 10^{-5}$ | 0.005 mol % | |
| $Pt\text{-}BuCy_2$ | 16.0 mg | 254.39 | $6.29 \cdot 10^{-5}$ | 0.02 mol % | |
| $H_2O$ | 290 mL | | | | |

A 1-L Schlenk flask equipped with a spherical stirrer bar was charged with 50 g of boronic acid 2 (1.1 equiv), 30.7 g of $Na_2CO_3$ (1.0 equiv) and and 46 g of the aryl chloride 1. The flask was transferred into a glovebox, where 4.0 mg of $Pd(OAc)_2$ (1.78·10-5, 0.005 mol %) and 16.0 mg of the ligand $PtBuCy_2$ ($6.29 \cdot 10^{-5}$, 0.02 mol %, Pd:L=1:4) were added into the solid aryl chloride 1. The flask was then transferred outside, where 290 mL of $H_2O$ were added under a flow of Ar. The flask was finally heated in an oil bath at 100° C. for 8 h. After this time the mixture was diluted with 100 mL of brine and subsequently extracted with EtOAc (2×100 mL) and the combined organic phases were dried over $MgSO_4$, filtered and then analyzed by GC.

General Procedure for Boscalid Three-Step One-Pot Synthesis:

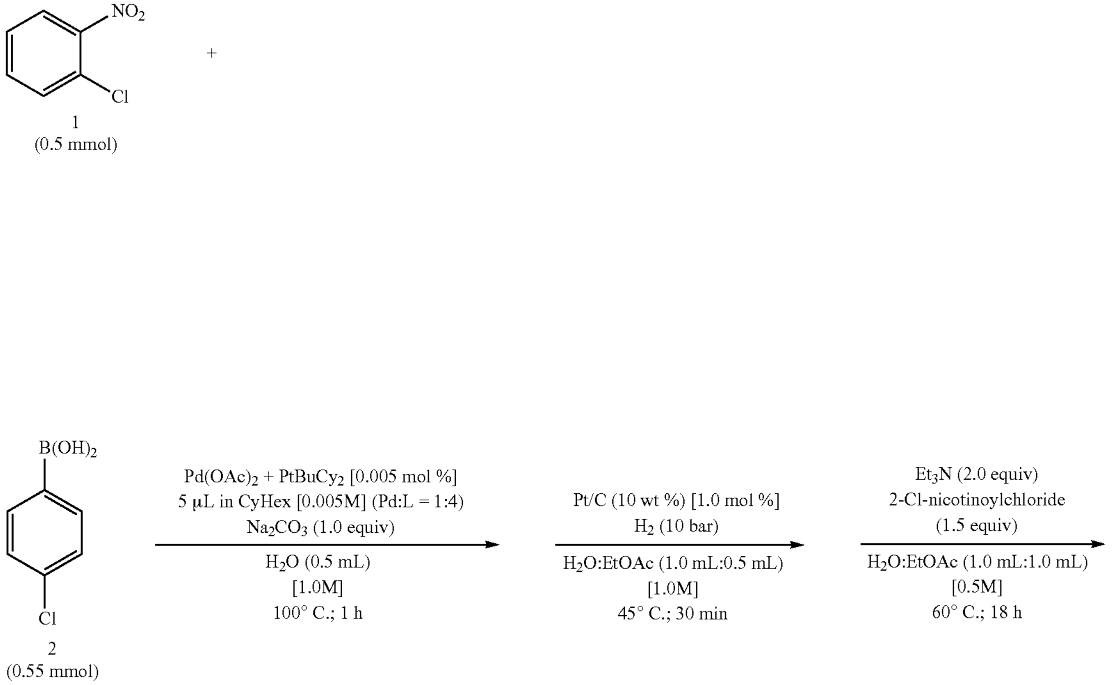

1 (0.5 mmol)

2 (0.55 mmol)

-continued

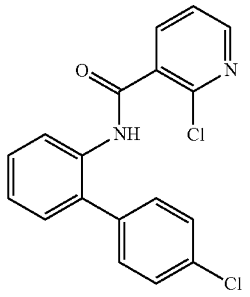

Boscalid

| | wt | Mw (g/mol) | mmol | eq | V |
|---|---|---|---|---|---|
| 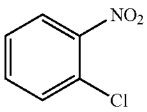 | 79 mg | 157.55 | 0.5 | 1 | |
| 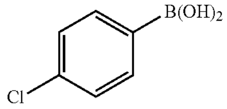 | 86 mg | 156.37 | 0.55 | 1.1 | — |
| $Na_2CO_3$ | 53 mg | 106 | 0.5 | 1 | |
| $Pd(OAc)_2$ + $PtBuCy_2$ | 0.5 mL | | 0.0005 | 0.005 mol % | µL in CyHex |
| $H_2O$ | | | | | |
| 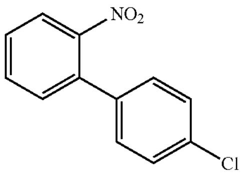 | ~110 mg | 233.65 | ~0.47 | 1 | |
| Pt/C | 10 mg | | 0.005 | 1 mol % | |
| $H_2O$:EtOAc | 1.0:0.5 mL | | | | |
| 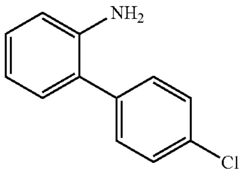 | ~90 mg | 203.65 | ~0.47 | 1 | |
| $Et_3N$ | | | 1.0 | 2 | 0.14 mL |
| 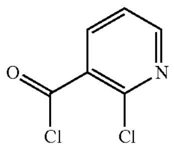 | 133 mg | 176 | 0.75 | 1.5 | |
| $H_2O$:EtOAc | | | | | |

In a glovebox, a 2 mL_pressure tube equipped with a spherical stirrer bar was charged with 86 mg of boronic acid 2 (1.1 equiv), 53 mg of $Na_2CO_3$ (1.0 equiv) and 5 µL of a 0.005 M solution of $Pd(OAc)_2$+$PtBuCy_2$ (Pd:L=1:4) in cyclohexane and 79 mg of the aryl chloride 1. The tube was capped and transferred outside the glovebox, where 0.5 mL of $H_2O$ were added under a flow of Ar. The vial was heated in an oil bath at 100° C. for 1 h. After this time, the reaction mixture was cooled down to rt and was filtered through a pad of activated charcoal to remove Pd catalyst. The mixture in the pressure tube was transferred into a 10 mL vial equipped with a stirrer bar and a bended needle on the septum (~110 mg of product 3), filtering it through a pad of celite. The pressure tube was rinsed with 0.5 mL of water and 0.5 mL of EtOAc. Subsequently, the vial was charged with 10 mg of Pt/C (10 wt %, 1 mol %) and the crimp cap was closed. The vial was placed in a TALL PREMEX autoclave and charged with 10 bar of $H_2$. The autoclave was then placed at 45° C. for 30 min. After this time, the autoclave was cooled to rt and the vial was filtered over a pad of celite to remove the Pt/C catalyst. The vial was rinsed with 0.5 mL of EtOAc. Subsequently, the vial was charged with 0.14 mL of $Et_3N$ (2.0 equiv) and the mixture was left stirring gently at rt for 10 min. After this time, the vial was quickly opened and 133 mg of 2-chloronicotinoyl chloride (1.5 equiv) was added inside and the vial was left stirring at 60° C. for 18 h. The reaction was monitored by TLC to follow the full consumption of the starting material. The mixture was the cooled down and extracted with EtOAc (3×2.0 mL) and brine (5.0 mL). After drying it over $MgSO_4$ and filtering, the mixture was concentrated in vacuo. Finally, the product was purified by column chromatography (form petrol ether:ethyl acetate=95:5 to petrol ether:ethyl acetate=60:40) to yield 130.2 mg of white solid, characterized as Boscalid® by 1H and 13C NMR spectroscopy, X-Ray analysis as well as HRMS analysis. The results fit the previously reported data for Boscalid®.

General Procedure for Xemium Three-Step One-Pot Synthesis:

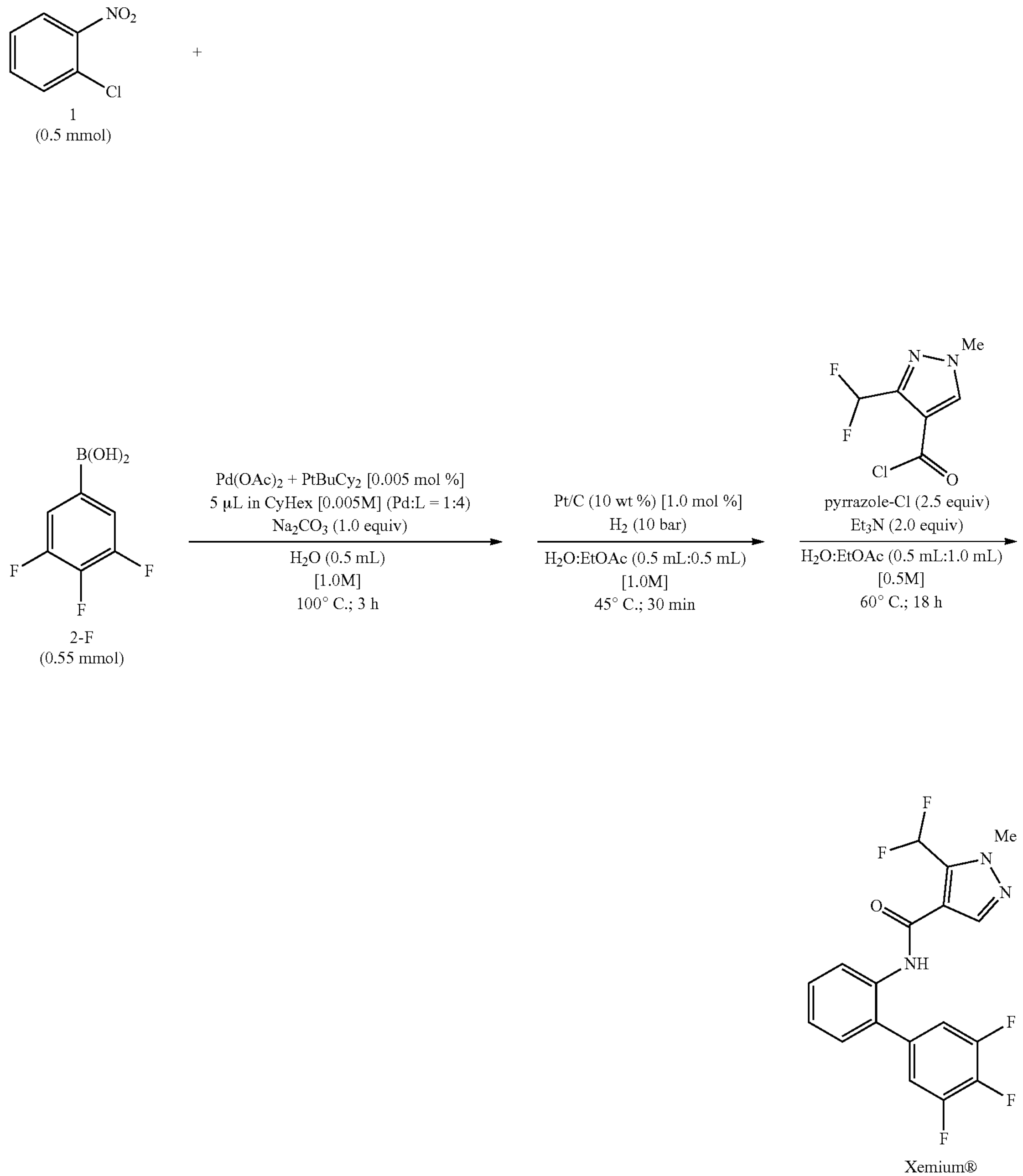

1
(0.5 mmol)

2-F
(0.55 mmol)

Xemium®

| | wt | Mw (g/mol) | mmol | eq | V |
|---|---|---|---|---|---|
| 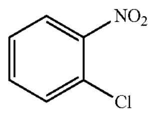 | 79 mg | 157.55 | 0.5 | 1 | |
| 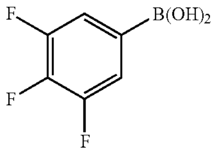 | 97 mg | 175.90 | 0.55 | 1.1 | — |
| $Na_2CO_3$ | 53 mg | 106 | 0.5 | 1 | |
| $Pd(OAc)_2$ + $PtBuCy_2$ | 0.5 mL | | 0.0005 | 0.005 mol % | 5 µL in CyHex |
| $H_2O$ | | | | | |
| 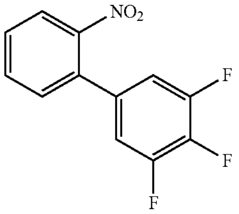 | ~110 mg | 233.65 | ~0.47 | 1 | |
| Pt/C | 10 mg | | | 1 mol % | |
| $H_2O$:EtOAc | 0.5:0.5 mL | | 0.005 | | |
| 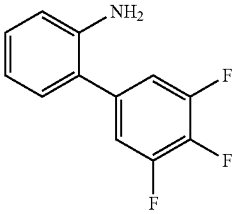 | ~90 mg | 223.20 | -0.47 | 1 | |
| $Et_3N$ | | | 1.0 | 2 | 0.14 mL |
| 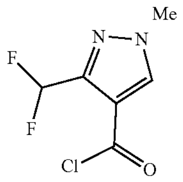 | 244 mg | 194.56 | 1.25 | 2.5 | |
| $H_2O$:EtOAc | 0.5:1.0 mL | | | | |

In a glovebox, a 2 mL_pressure tube equipped with a spherical stirrer bar was charged with 97 mg of boronic acid 2-F (1.1 equiv), 53 mg of $Na_2CO_3$ (1.0 equiv) and 5 µL of a 0.005 M solution of $Pd(OAc)_2$+$PtBuCy_2$ (Pd:L=1:4) in cyclohexane and 79 mg of the aryl chloride 1. The tube was capped and transferred outside the glovebox, where 0.5 mL of $H_2O$ were added under a flow of Ar. The vial was heated in an oil bath at 100° C. for 3 h. The mixture in the pressure tube was transferred into a 10 mL vial equipped with a stirrer bar and a bended needle on the septum (~110 mg of product 3-F). The pressure tube was rinsed with 0.5 ml of water and 0.5 mL of EtOAc. Subsequently, the vial was charged with 10 mg of Pt/C (10 wt %, 1 mol %) and the crimp cap was closed. The vial was placed in a HEL CAT 7 autoclave and charged with 10 bar of $H_2$. The autoclave was then placed at 45° C. for 30 min. After this time, the autoclave was cooled to rt and the vial was filtered over a pad of celite to remove the Pt/C catalyst. The vial was rinsed with 0.5 mL of EtOAc. Subsequently, the vial was charged with 0.14 mL of $Et_3N$ (2.0 equiv) and the mixture was left stirring gently at rt for 10 min. After this time, the vial was quickly opened and 107 mg of PO-539 (1.1 equiv) was added inside and the vial was left stirring at 60° C. The reaction was monitored by TLC to follow the full consumption of the starting material. The mixture was the cooled down and extracted with EtOAc (3×1.0 mL). After drying it over $MgSO_4$ and filtering, the mixture was concentrated in vacuo. Finally, the product was purified by column chromatography (form petrol ether:ethyl acetate=95:5 to petrol ether:ethyl acetate=60:40) to yield 126 mg of white solid, characterized as Xemium® by $^1H$ and $^{13}C$ NMR spectroscopy, X-Ray analysis as well as HRMS analysis. The results fit the previously reported data for Xemium®.

Comparative Experiments Using Aryl-Substituted Phosphine Ligands:

Investigation on Aryl Substituted Phosphines:

using $Pd(OAc)_2$+$PPh_3$ (0.005 mol %):

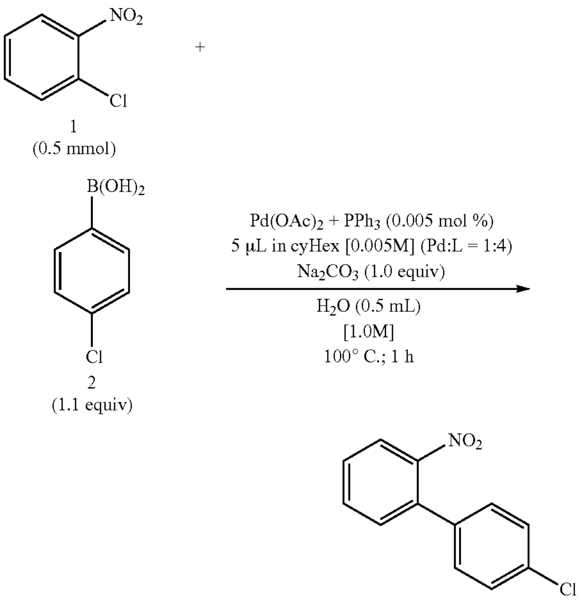

1 (0.5 mmol)

2 (1.1 equiv)

3
conversion 25%
yield 2% using $Pd(OAc)_2$+$PCy_2Ph$ (0.005 mol %):

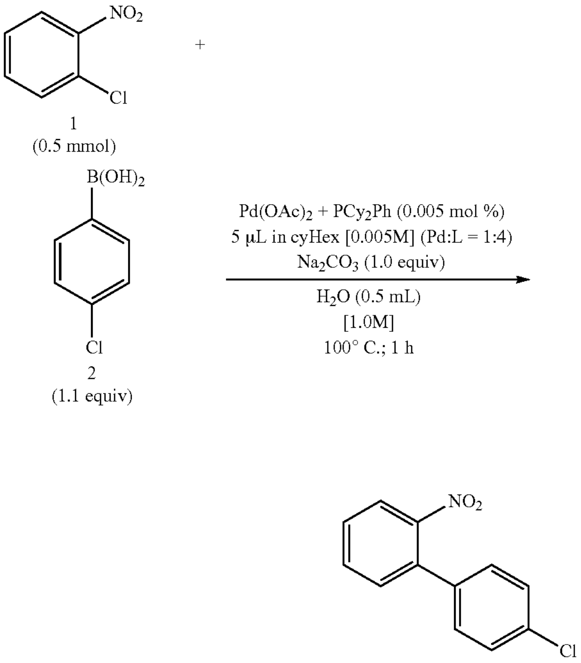

1 (0.5 mmol)

2 (1.1 equiv)

3
conversion 53%
yield 33% using $Pd(OAc)_2$+$PCyPh_2$ (0.005 mol %):

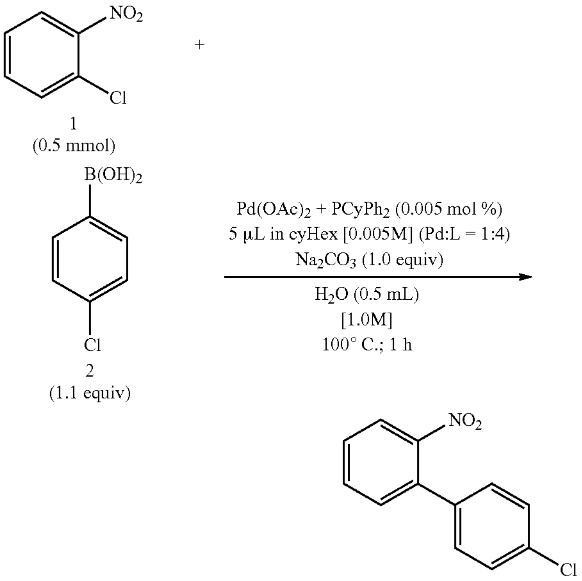

1 (0.5 mmol)

2 (1.1 equiv)

3
conversion 30%
yield 4% using $Pd(OAc)_2$+SPhos (0.005 mol %) [Buchwald ligand]:

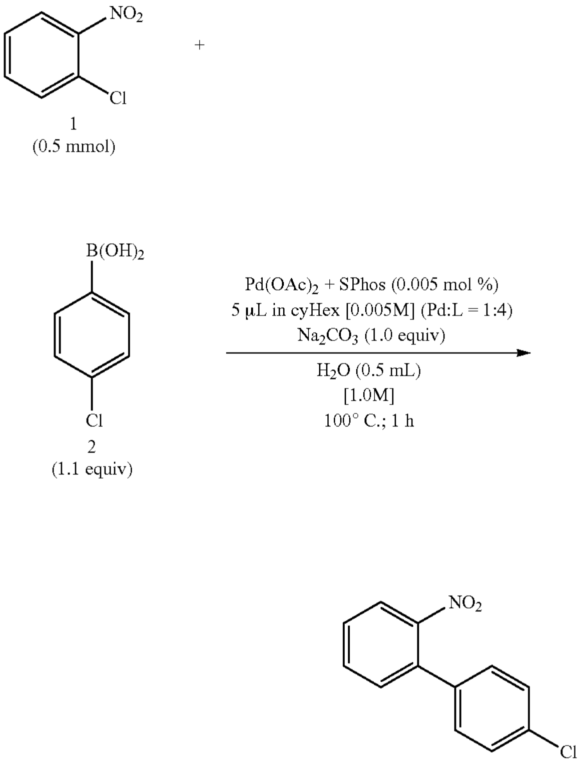

1 (0.5 mmol)

2 (1.1 equiv)

3
conversion 36%
yield 16%

The invention claimed is:

1. A process for preparing a substituted biphenyls biphenyl of the formula I

I

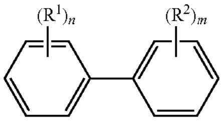

in which the substituents are each defined as follows:

$R^1$ is cyano, nitro, F, Cl, C1-C4-alkyl, C1-C4-haloalkyl, C3-C10-cycloalkyl which may carry 1, 2, 3 or 4 C1-C4-alkyl substituents; C3-C10-halocycloalkyl, C1-C6-alkoxy, C1-C6-haloalkoxy, C1-C6-alkylcarbonyl, C1-C6-haloalkylcarbonyl, C1-C6-alkoxycarbonyl, or C1-C6-haloalkoxycarbonyl;

$R^2$ is cyano, nitro, F, Cl, C1-C4-alkyl, C1-C4-haloalkyl, C3-C10-cycloalkyl which may carry 1, 2, 3 or 4 C1-C4-alkyl substituents; C3-C10-halocycloalkyl, C1-C6-alkoxy, C1-C6-haloalkoxy, C1-C6-alkylcarbonyl, C1-C6-haloalkylcarbonyl, C1-C6-alkoxycarbonyl, or C1-C6-haloalkoxycarbonyl; and n is 0, 1, 2, or 3, where, in case that n is 2 or 3, the $R^1$ radicals may have identical or different definitions; and m is 0, 1, 2, or 3, where, in case that n is 2 or 3, the $R^2$ radicals may have identical or different definitions which comprises reacting a compound of formula II

II

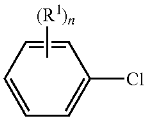

in which $R^1$ and n is as defined as above, in the presence of a base and a palladium catalyst, where the palladium catalyst is introduced into the reaction in the form of a palladium source and a phosphorus ligand of formula III or a salt thereof

III

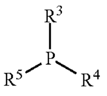

in which $R^3$ is C3-C18-alkyl or C3-C10-cycloalkyl which is connected to the phosphor atom at a secondary or tertiary carbon atom of the C3-C18-alkyl or C3-C10-cycloalkyl substituent;

$R^4$ is C1-C18-alkyl or C3-C10-cycloalkyl;

and $R^5$ is C1-C18-alkyl or C3-C10-cycloalkyl; or a palladium complex containing at least one phosphorus ligand of the formula III as defined above or a salt thereof;

with water as solvent, wherein a total solvent comprises at least 95 wt.-% water based on the total solvent without the use of an additional surfactant or phase transfer catalyst with an organoboron compound of formula IV

IV

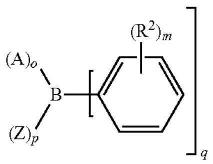

wherein $R^2$ and m are as defined as above and the compound of formula IV is selected from the group consisting of (i) boronic acids with o=0, p=2; q=1 and Z=hydroxyl groups, or their trimers;

(ii) boronic acid derivates with o=0, p=2; q=1 and Z=halogen; C1-C4-alkyl, C1-C6-alkoxy or C6-C10-aryloxy;

(iii) boronic acids or boronic acid derivatives with o=0, p=1; q=2 and Z=hydroxy, halogen, C1-C4-alkyl, C1-C6-alkoxy or C6-C10-aryloxy;

(iv) mixed boronic acids or boronic acid derivatives with 0=1, p=1; q=1, A=C1-C4-alkyl and Z=hydroxy, halogen, C1-C4-alkyl, C1-C6-alkoxy or C6-C10-aryloxy;

(v) cyclic boronic esters with o=0, p=2 and q=1, wherein the two Z groups form together a bridging group —O—(CH2)r-O—, wherein r is 2 or 3, so that the two Z groups, together with the boron atom to which they are attached, form a 5- or 6-membered ring, where the CH2 groups are optionally substituted by one or two C1-C4-alkyl groups;

(vi) boronates with o=0, p=3, q=1 and Z=hydroxyl, halogen, C1-C4-alkyl, C1-C6-alkoxy or C6-C10-aryloxy, and accompanied by a cation which compensates the negative charge of the boronate anion;

(vii) triarylboranes with o=0, p=0 and q=3;

(viii) tetraarylborates with o=0, p=0 and q=4, and accompanied by a cation which compensates the negative charge of the borate anion; and where the reaction is carried out at a temperature of from 60 to 150° C.

2. The process according to claim 1, wherein the palladium catalyst is 0.01 to 0.001 mol % relating to the compound of formula II.

3. The process according to claim 1, wherein the solvent comprises less than 5 wt.-% of organic solvents, which are only partially or not miscible with water, based on the total solvent.

4. The process according to claim 1, wherein the total solvent comprises at least 98 wt.-% water based on the total solvent.

5. The process according to claim 1, wherein the solvent comprises less than 2 wt.-% of organic solvents, which are only partially or not miscible with water, based on the total solvent.

6. The process according to claim 1, wherein the solvent comprises no other solvent miscible with water.

7. The process according to claim 1, wherein no additional organic solvent is present.

8. The process according to claim 1, wherein in the formula III $R^3$ and $R^4$=cyclohexyl and $R^5$=tertbutyl.

9. The process according to claim 1, wherein in the formula I, $R^1$=nitro, n=1, $R^2$=Cl and m=1.

10. The process according to claim 1, wherein formula I is 2-nitro-4'-Cl-biphenyl.

11. The process according to claim 1, wherein in formula IV, o=0, Z=OH, p=1, $R^2$=para-chloro, m=1, and q=2.

* * * * *